(12) United States Patent
Yamamoto et al.

(10) Patent No.: US 8,097,349 B2
(45) Date of Patent: Jan. 17, 2012

(54) NITROGEN CONTAINING HETEROCYCLE DERIVATIVE AND ORGANIC ELECTROLUMINESCENT ELEMENT USING THE SAME

(75) Inventors: Hiroshi Yamamoto, Sodegaura (JP);
Masahide Matsuura, Sodegaura (JP);
Mineyuki Kubota, Sodegaura (JP);
Masahiro Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 12/662,251

(22) Filed: Apr. 7, 2010

(65) Prior Publication Data

US 2010/0193773 A1 Aug. 5, 2010

Related U.S. Application Data

(63) Continuation of application No. 10/547,312, filed as application No. PCT/JP2004/000682 on Jan. 27, 2004.

(30) Foreign Application Priority Data

Mar. 13, 2003 (JP) ................................ 2003-067847

(51) Int. Cl.
*H01L 51/54* (2006.01)

(52) U.S. Cl. ........ 428/690; 428/917; 313/504; 313/506; 257/40; 257/103; 257/E51.05; 252/301.16; 548/304.4; 548/304.7; 546/273.4; 546/274.1

(58) Field of Classification Search .................. None
See application file for complete search history.

(56) References Cited

U.S. PATENT DOCUMENTS

| 5,645,948 A | 7/1997 | Shi et al. |
| 6,124,463 A | 9/2000 | Beck et al. |
| 6,509,109 B1 | 1/2003 | Nakamura et al. |
| 2002/0028329 A1 | 3/2002 | Ise et al. |
| 2002/0037427 A1 | 3/2002 | Taguchi |
| 2002/0055014 A1 | 5/2002 | Okada et al. |
| 2002/0063517 A1 | 5/2002 | Hosokawa |
| 2003/0165715 A1 | 9/2003 | Yoon et al. |
| 2004/0023060 A1 | 2/2004 | Kim et al. |

FOREIGN PATENT DOCUMENTS

| JP | 10-092578 | 4/1998 |
| JP | 2000-095766 | 4/2000 |
| JP | 2001-288172 | 10/2001 |
| JP | 2002-038141 | 2/2002 |
| JP | 2002-047274 | 2/2002 |
| JP | 2002-124385 | 4/2002 |
| JP | 2002-231452 | 8/2002 |
| JP | 2002-231455 | 8/2002 |
| WO | WO 00/01675 | 1/2000 |
| WO | WO 02/088274 | 11/2002 |
| WO | WO 03/060956 | 7/2003 |

OTHER PUBLICATIONS

Kauffman, J.M. et al., "Synthesis and Photophysical Properties of Fluroescent 2-Aryl-1,3-dialkylbenzimidazolium Ions and a 1-Alkyl-2-arylbenzimidazole with Excited State Intramolecular Proton-Transfer," Journal of Heterocyclic Chemistry, vol. 31, No. 4, 1994, pp. 957-965.

*Primary Examiner* — D Lawremce Tarazano
*Assistant Examiner* — Michael H Wilson
(74) *Attorney, Agent, or Firm* — Oblon, Spivak, McClelland, Maier & Neustadt, L.L.P.

(57) ABSTRACT

A novel derivative of heterocyclic compound having nitrogen atom with a structure made by bonding special groups to benzimidazole, a material for an organic electroluminescence (EL) device comprising the derivative of heterocyclic compound having nitrogen atom and an organic electroluminescence device comprising at least one organic compound layer containing a light emitting layer sandwiched between a pair of electrodes, wherein the device contains the derivative of heterocyclic compound having nitrogen atom. An organic EL device achieving elevation of luminance and of efficiency in light emission even under low driving voltage is obtainable by an employment of the derivative of heterocyclic compound having nitrogen atom for at least one layer composing organic compound layers of the EL device.

9 Claims, No Drawings

NITROGEN CONTAINING HETEROCYCLE DERIVATIVE AND ORGANIC ELECTROLUMINESCENT ELEMENT USING THE SAME

The present application is a Continuation Application of Ser. No. 10/547,312, filed Aug. 30, 2005, which was a national stage entry of International Application PCT/JP2004/000682, filed Jan. 27, 2004, which claims priority of Japanese Patent Application Nos. 2003-067847, filed Mar. 13, 2003.

TECHNICAL FIELD

The present invention relates to a novel nitrogen-containing heterocycle derivative, i.e., a novel derivative of heterocyclic compound having nitrogen atom and to an organic electroluminescent element (an electroluminescent element will be referred to as an electroluminescence device, hereinafter) which utilizes the novel compound. More particularly, the present invention relates to a derivative of heterocyclic compound having nitrogen atom useful as constituting component of an organic electroluminescence ("electroluminescence" will be occasionally referred to as "EL", hereinafter) device, i.e., an organic EL device achieving elevation of luminance and of efficiency in light emission even under low driving voltage in accordance with an employment of the derivative of heterocyclic compound having nitrogen atom for at least one layer composing organic compound layers of the EL device.

BACKGROUND ART

Organic EL devices which utilize organic substances are expected to be useful for application as an inexpensive full color display device of the solid light emission type having a great size and various developments on the organic EL devices are being conducted. In general, an organic EL device has a construction comprising a light emitting layer and a pair of electrodes sandwiching the light emitting layer. The light emission of the organic EL device is a phenomenon in which, when an electric field is applied between the two electrodes, electrons are injected from the cathode side and holes are injected from the anode side, the electrons are recombined with the holes in the light emitting layer to form an excited state, and energy generated when the excited state returns to the ground state is emitted as light.

As compared with an inorganic light emitting diode, conventional organic EL devices requires high driving voltage and only exhibited low luminance or low efficiency of light emission. Moreover, characteristic degradation of the conventional organic EL devices was also extravagant and as a result, they were not practically used. Although recent organic EL devices are improved step by steps, it has been still demanded to develop organic EL devices operable at low driving voltage, with excellent luminance and favorable efficiency of light emission.

Resolving the above problems, for example, U.S. Pat. No. 5,645,948 discloses an organic EL device with the use of a compound having benzimidazole structure as an light emitting material describing that the organic EL device emits light with a luminance of 200 nit at a voltage of 9 V. Further, Japanese Unexamined Patent Application Laid-Open No. 2002-38141 discloses a compound having benzimidazole ring and anthracene skeleton. However, an organic EL device with further enhanced luminance and with further improved efficiency of light emission than the organic EL device with the use of the above compounds is required.

DISCLOSURE OF THE INVENTION

The object of the present invention is to provide a novel derivative of heterocyclic compound having nitrogen atom useful as a constitutional component of an organic EL device. Another object of the present invention is to provide an organic EL device achieving elevation of luminance and of efficiency in light emission in accordance with an employment of the derivative of heterocyclic compound having nitrogen atom for at least one layer composing organic compound layers of the EL device. As a result of intensive researches and studies to achieve the above object by the present inventors, a derivative of heterocyclic compound having nitrogen atom was found to be a novel compound with specific structure useful as a material for an organic El device. Further, employing the compound as a component of at least one layer (in particular, electron injecting layer) in organic compound layers of an organic EL device was also found enabling to achieve elevation of luminance and of efficiency in light emission. Such being the case, the present invention has been accomplished on the basis of the foregoing findings and information.

Namely, the present invention provides a derivative of heterocyclic compound having nitrogen atom represented by any one of general formulae (I), (II) or (III) below.

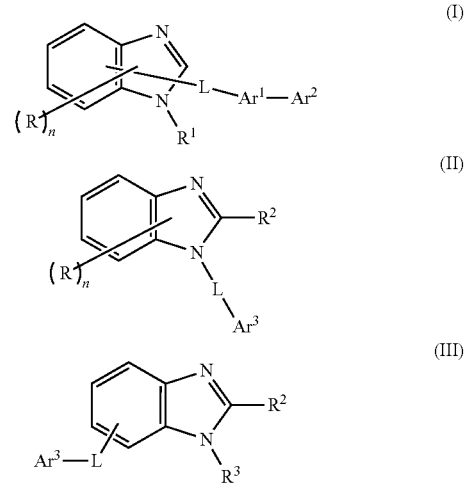

wherein R represents a hydrogen atom, an aryl group having 6 to 60 carbon atoms and may have a substituent, a pyridyl group which may have a substituent, or a quinolyl group which may have a substituent; an alkyl group having 1 to 20 carbon atoms and may have a substituent or an alkoxy group having 1 to 20 carbon atoms and may have a substituent; n represents an integer of 0 to 4;

$R^1$ represents an aryl group having 6 to 60 carbon atoms and may have a substituent, a pyridyl group which may have a substituent, or a quinolyl group which may have a substituent; an alkyl group having 1 to 20 carbon atoms and may have a substituent or an alkoxy group having 1 to 20 carbon atoms and may have a substituent;

$R^2$ and $R^3$ each independently represents a hydrogen atom, an aryl group having 6 to 60 carbon atoms and may have a substituent, a pyridyl group which may have a substituent, or a quinolyl group which may have a substituent; an alkyl group having 1 to 20 carbon atoms and may have a substituent or an alkoxy group having 1 to 20 carbon atoms and may have a substituent;

L represents an arylene group having 6 to 60 carbon atoms and may have a substituent, a pyridinylene group which may have a substituent, a quinolinylene group which may have a substituent or a fluorenylene group which may have a substituent;

$Ar^1$ represents an arylene group having 6 to 60 carbon atoms and may have a substituent, a pyridinylene group which may have a substituent, or a quinolinylene group which may have a substituent;

$Ar^2$ represents an aryl group having 6 to 60 carbon atoms and may have a substituent, a pyridyl group which may have a substituent, or a quinolyl group which may have a substituent; an alkyl group having 1 to 20 carbon atoms and may have a substituent or an alkoxy group having 1 to 20 carbon atoms and may have a substituent;

$Ar^3$ represents an aryl group having 6 to 60 carbon atoms and may have a substituent, a pyridyl group which may have a substituent, or a quinolyl group which may have a substituent; an alkyl group having 1 to 20 carbon atoms and may have a substituent, an alkoxy group having 1 to 20 carbon atoms and may have a substituent; or a group represented by —$Ar^1$—$Ar^2$, in which both $Ar^1$ and $Ar^2$ are the same as the above description.

Also, the present invention provides a material for the organic EL device comprising the above derivative of heterocyclic compound having nitrogen atom.

Moreover, the present invention provides an organic EL device comprising at least one of organic compound layers including a light emitting layer sandwiched between a pair of electrode, wherein the organic EL device comprises the foregoing derivative of heterocyclic compound having nitrogen atom of the invention in at least one of the organic compound layers.

THE PREFERRED EMBODIMENT TO CARRY OUT THE INVENTION

The derivatives of heterocyclic compound having nitrogen atom of the present invention (referred to as "compound of the present invention" below) are represented by any one of the above general formulae (I), (II) or (III).

In general formulae (I) to (III), R represents a hydrogen atom, an aryl group having 6 to 60 carbon atoms and may have a substituent, a pyridyl group which may have a substituent, or a quinolyl group which may have a substituent; an alkyl group having 1 to 20 carbon atoms and may have a substituent or an alkoxy group having 1 to 20 carbon atoms and may have a substituent.

The aryl group having 6 to 60 carbon atoms is preferably an aryl group having 6 to 40 carbon atoms, more preferably an aryl group having 6 to 20 carbon atoms. Specific examples of the aryl group having 6 to 20 carbon atoms include phenyl group, naphthyl group, anthryl group, phenanthryl group, naphthacenyl group, chrysenyl group, pyrenyl group, biphenyl group, terphenyl group, tolyl group, t-butylphenyl group, (2-phenylpropyl)phenyl group, fluoranthenyl group, fluorenyl group, monovalent group consisting of spirobifluorene, perfluorophenyl group, perfluoronaphthyl group, perfluoro anthryl group, perfluorinated biphenyl group, monovalent group consisting of 9-phenylanthracene, monovalent group consisting of 9-(1'-naphthyl) anthracene, monovalent group consisting of 9-(2'-naphthyl) anthracene, monovalent group consisting of 6-phenylchrysene, monovalent group consisting of 9-[4-(diphenylamino) phenyl]anthracene, etc. Among these, phenyl group, naphthyl group, biphenyl group, terphenyl group, 9-(10-phenyl) anthryl group, 9-[10-(1'-naphthyl)] anthryl group, 9-[10-(2'-naphthyl)]anthryl group or so is preferable.

The alkyl group having 1 to 20 carbon atoms is preferably an alkyl group having 1 to 6 carbon atoms. Specific examples of the alkyl group having 1 to 6 carbon atoms include methyl group, ethyl group, propyl group, butyl group, pentyl group, hexyl group, etc. The alkyl group having 3 or more carbon atoms may be linear, cyclic or branched.

The alkoxy group having 1 to 20 carbon atoms is preferably an alkoxy group having 1 to 6 carbon atoms. Specific examples of the alkoxy group having 1 to 6 carbon atoms include methoxy group, ethoxy group, propoxy group, butoxy group, pentyloxy group, hexyloxy group, etc. The alkoxy group having 3 or more carbon atoms may be linear, cyclic or branched.

Examples of the substituent represented by R include a halogen atom, an alkyl group having 1 to 20 carbon atoms and may have a substituent, an alkoxy group having 1 to 20 carbon atoms and may have a substituent, an aryloxy group having 6 to 40 carbon atoms and may have a substituent, a diarylamino group having 12 to 80 carbon atoms and may have a substituent, an aryl group having 6 to 40 carbon atoms and may have a substituent, a heteroaryl group having 3 to 40 carbon atoms and may have a substituent, etc.

Examples of the halogen atom include fluorine atom, chlorine atom, bromine atom and iodine atom.

Similar groups with the above description are exemplified as the alkyl groups having 1 to 20 carbon atoms, the alkoxy groups having 1 to 20 carbon atoms and the aryl groups having 6 to 40 carbon atoms.

Specific examples of the aryloxy group having 6 to 40 carbon atoms include phenoxy group, biphenyl oxy group, etc.

Specific examples of the heteroaryl group having 3 to 40 carbon atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, etc.

n represents an integer of 0 to 4 and is preferably 0 to 2.

In general formula (I), $R^1$ represents an aryl group having 6 to 60 carbon atoms and may have a substituent, a pyridyl group which may have a substituent, or a quinolyl group which may have a substituent; an alkyl group having 1 to 20 carbon atoms and may have a substituent or an alkoxy group having 1 to 20 carbon atoms and may have a substituent.

Specific examples, preferable numbers of carbon atoms and substituents of the each above groups are the same as those described about the above R.

In general formulae (II) and (III), $R^2$ and $R^3$ each independently represents a hydrogen atom, an aryl group having 6 to 60 carbon atoms and may have a substituent, a pyridyl group which may have a substituent, or a quinolyl group which may have a substituent; an alkyl group having 1 to 20 carbon atoms and may have a substituent or an alkoxy group having 1 to 20 carbon atoms and may have a substituent.

Specific examples, preferable numbers of carbon atoms and substituents of the each above groups are the same as those described about the above R.

In general formulae (I) to (III), L represents an arylene group having 6 to 60 carbon atoms and may have a substituent, a pyridinylene group which may have a substituent, a quinolinylene group which may have a substituent or a fluorenylene group which may have a substituent Arylene group having 6 to 40 carbon atoms is preferable as those having 6 to 60 carbon atoms, and arylene group having 6 to 20 carbon atoms is more preferable, and further, concrete examples include divalent groups formed by removing hydrogen atom from the aryl groups described about the above R. Substituents for each group represented by L are the same as described about the above R.

L preferably represents a group selected from the following groups:

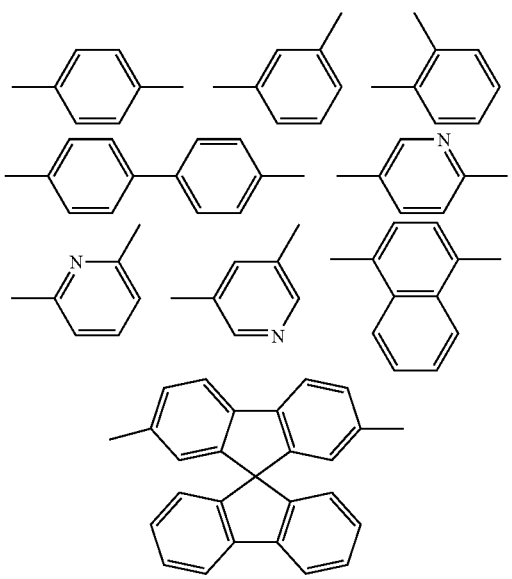

In general formula (I), Ar¹ represents an arylene group having 6 to 60 carbon atoms and may have a substituent, a pyridinylene group which may have a substituent, or a quinolinylene group which may have a substituent. Substituents for each groups represented by Ar¹ or Ar³ are the same as those described about the above R respectively.

Further, Ar¹ is preferably any one group selected from the condensed ring groups represented by the following general formulae (1) to (10):

(1)

(2)

(3)

(4)

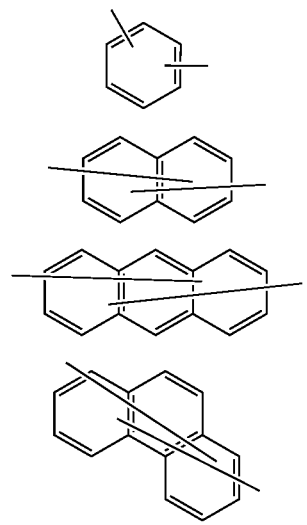

(5)

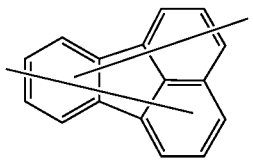

(6)

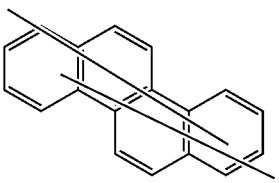

(7)

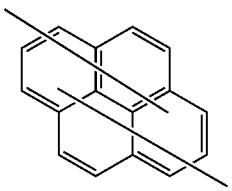

(8)

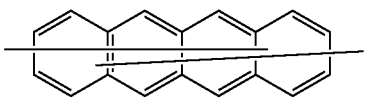

(9)

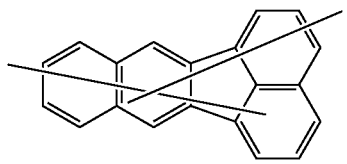

(10)

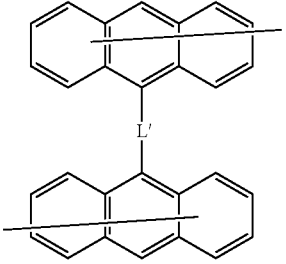

In general formulae (1) to (10), each condensed ring groups may be bonded with a bonding group of a halogen atom, an alkyl group having 1 to 20 carbon atoms and may have a substituent, an alkoxy group having 1 to 20 carbon atoms and may have a substituent, an aryloxy group having 6 to 40 carbon atoms and may have a substituent, an aryl group having 6 to 40 carbon atoms and may have a substituent, or a heteroaryl group having 3 to 40 carbon atoms and may have a substituent. When there are plural of bonding groups, the bonding group may be the same or different with each other. Specific examples of these groups are the same as the above description.

In general formula (10), L' represents a single bond or a group selected from the following groups:

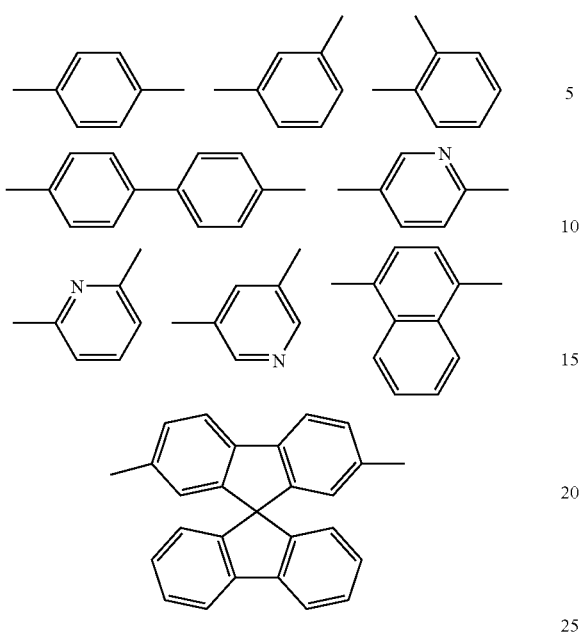
It is preferable that general formula (3) represented by $Ar^1$ is a condensed ring group represented by the following general formulae (11) to (25).
(11)
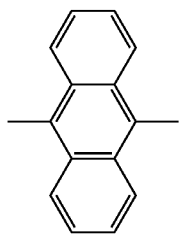
(12)
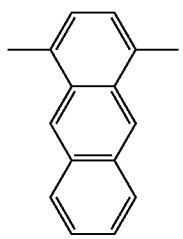
(13)
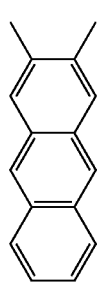
(14)
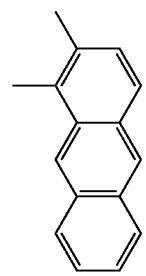
(15)
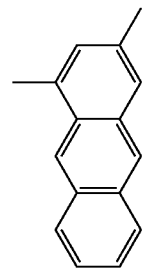
(16)
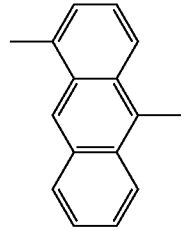
(17)
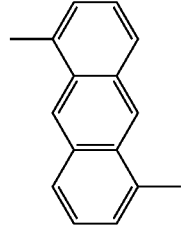
(18)
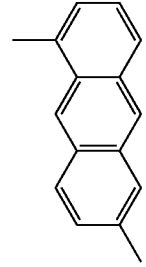
(19)

(20)

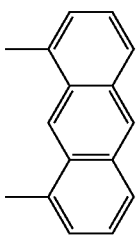

(21)

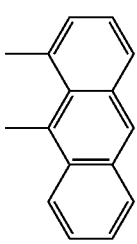

(22)

(23)

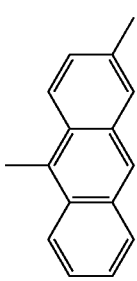

(24)

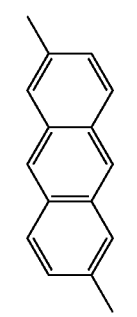

(25)

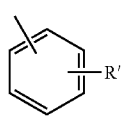

In general formulae (11) to (25), each condensed ring groups may be bonded with a bonding group of a halogen atom, an alkyl group having 1 to 20 carbon atoms and may have a substituent, an alkoxy group having 1 to 20 carbon atoms and may have a substituent, an aryloxy group having 6 to 40 carbon atoms and may have a substituent, an aryl group having 6 to 40 carbon atoms and may have a substituent, or a heteroaryl group having 3 to 40 carbon atoms and may have a substituent. When there are plural of bonding groups, the bonding group may be the same or different with each other. Specific examples of these groups are the same as the above description.

In general formula (I), $Ar^2$ represents an aryl group having 6 to 60 carbon atoms and may have a substituent, a pyridyl group which may have a substituent, or a quinolyl group which may have a substituent; an alkyl group having 1 to 20 carbon atoms and may have a substituent or an alkoxy group having 1 to 20 carbon atoms and may have a substituent.

Specific examples, preferable numbers of carbon atoms and substituents of the each above groups are the same as those described about the above R.

In general formula (II) and (III), $Ar^3$ represents an aryl group having 6 to 60 carbon atoms and may have a substituent, a pyridyl group which may have a substituent, or a quinolyl group which may have a substituent; an alkyl group having 1 to 20 carbon atoms and may have a substituent, an alkoxy group having 1 to 20 carbon atoms and may have a substituent; or a group represented by —$Ar^1$—$Ar^2$, in which both $Ar^1$ and $Ar^2$ are the same as the above description.

Specific examples, preferable numbers of carbon atoms and substituents of the each above groups are the same as those described about the above R.

Further, $Ar^3$ is preferably any one group selected from the condensed ring groups represented by the following general formulae (21) to (30):

(21)

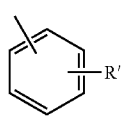

(22)

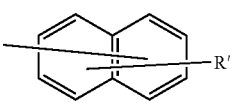

(23)

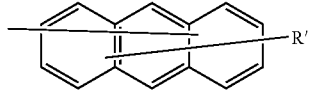

-continued

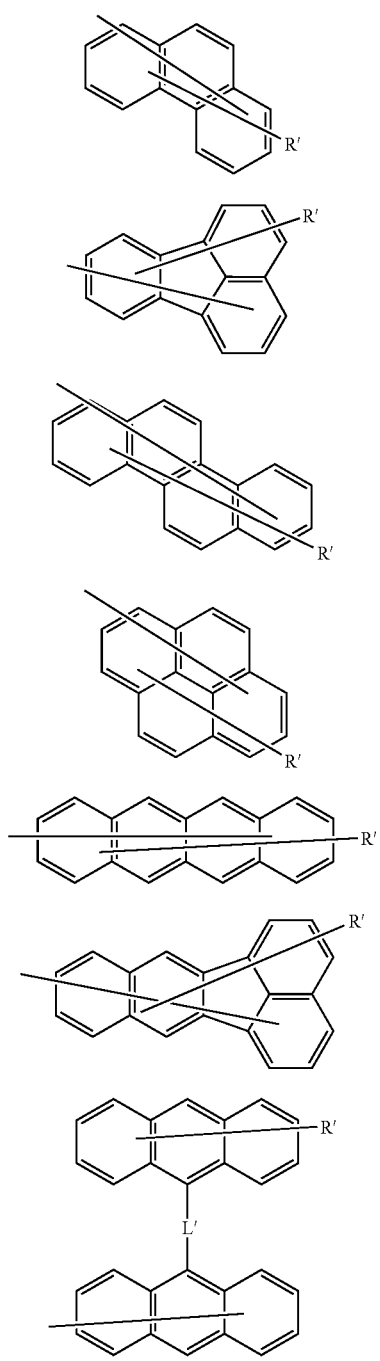

In general formulae (21) to (30), each condensed ring groups may be bonded with a bonding group of a halogen atom, an alkyl group having 1 to 20 carbon atoms and may have a substituent, an alkoxy group having 1 to 20 carbon atoms and may have a substituent, an aryloxy group having 6 to 40 carbon atoms and may have a substituent, an aryl group having 6 to 40 carbon atoms and may have a substituent, or a heteroaryl group having 3 to 40 carbon atoms and may have a substituent. When there are plural of bonding groups, the bonding group may be the same or different with each other. Specific examples of these groups are the same as the above description.

In general formula (30), L' is the same as the above description.

In general formulae (21) to (30), R' represents a hydrogen atom, an alkyl group having 1 to 20 carbon atoms and may have a substituent, an aryl group having 6 to 40 carbon atoms and may have a substituent or a heteroaryl group having 3 to 40 carbon atoms and may have a substituent. Specific examples of these groups are the same as the above description.

It is preferable that general formula (23) represented by Ar³ is a condensed ring group represented by the following general formulae (41) to (63).

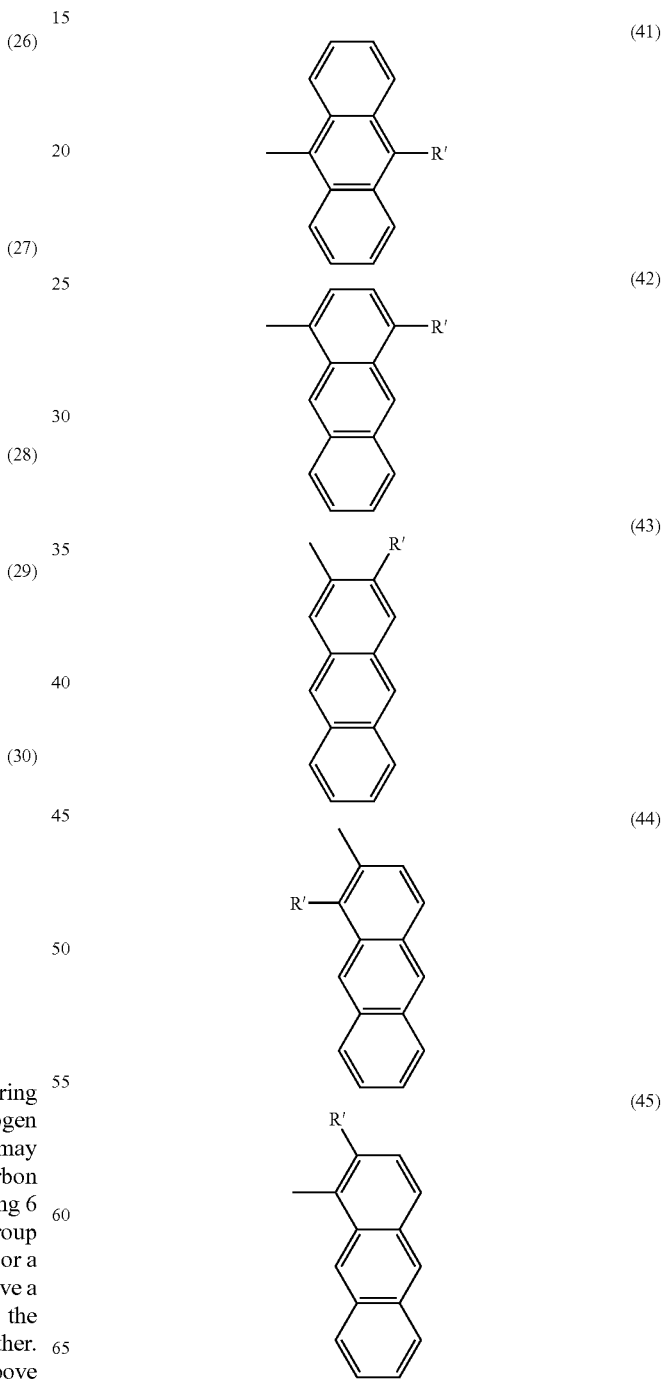

-continued
(46)
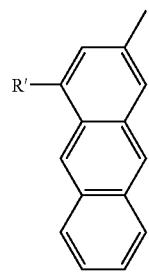
(47)
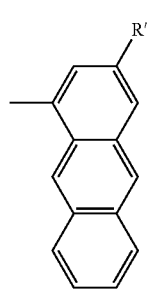
(48)
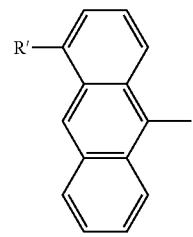
(49)
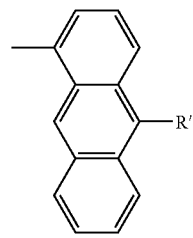
(50)
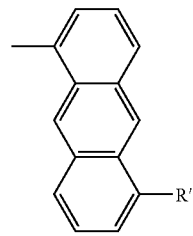
(51)
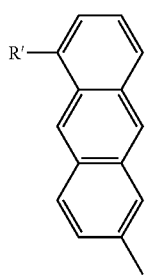
-continued
(52)
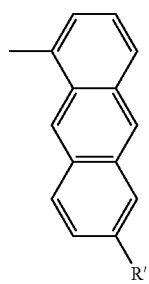
(53)
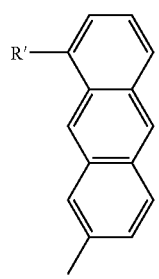
(54)
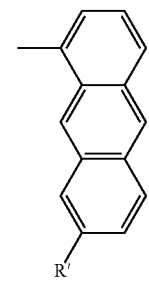
(55)
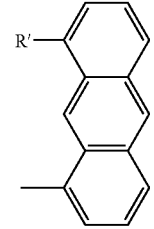
(56)
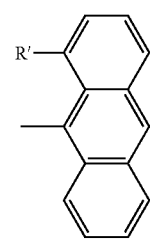
(57)
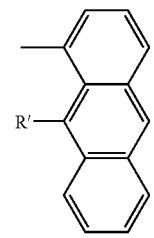

(58)
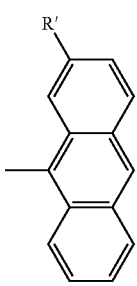

(59)
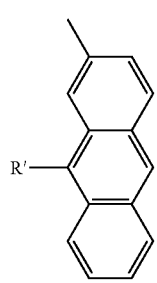

(60)
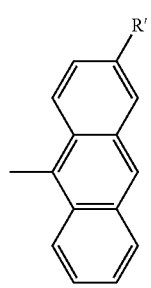

(61)
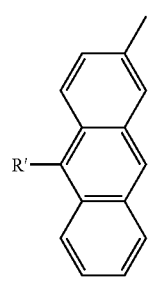

(62)
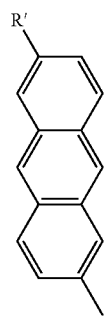

(63)
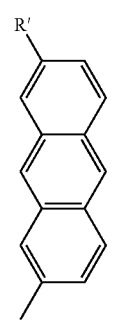

In general formulae (41) to (63), each condensed ring groups may be bonded with a bonding group of a halogen atom, an alkyl group having 1 to 20 carbon atoms and may have a substituent, an alkoxy group having 1 to 20 carbon atoms and may have a substituent, an aryloxy group having 6 to 40 carbon atoms and may have a substituent, an aryl group having 6 to 40 carbon atoms and may have a substituent, or a heteroaryl group having 3 to 40 carbon atoms and may have a substituent. When there are plural of bonding groups, the bonding group may be the same or different with each other. Specific examples of these groups are the same as the above description. R' is the same as in the case of the foregoing description.

Further, it is preferable that $Ar^2$ and $Ar^3$ each independently is a group selected from the following groups:

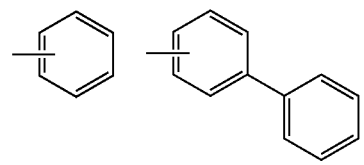

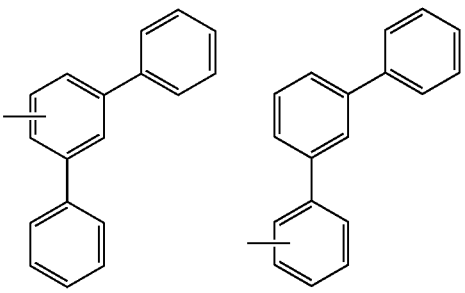

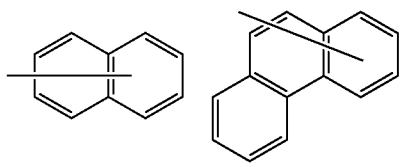

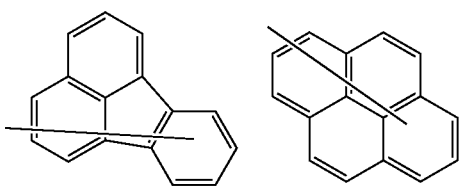

-continued

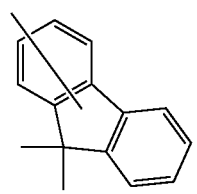

Specific examples of the novel derivative of heterocyclic compound having nitrogen atom represented by general formulae (I) to (III) of the present invention are as follows, however, the present invention is not limited to these typical compounds.

In the Table below, HAr represents compounds:

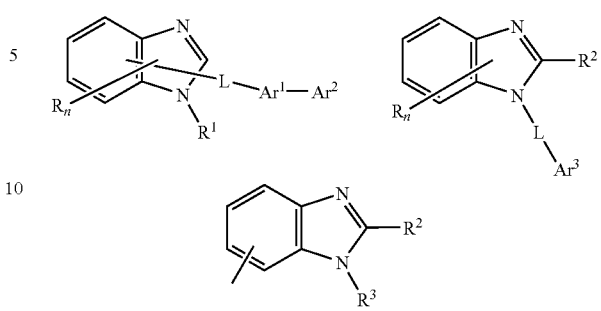

in general formulae (I) to (III).

| | HAr-L-Ar$^1$-Ar$^2$ | |
|---|---|---|
| | HAr | L |
| 1-1 | ![benzimidazole with phenyl and methyl] | ![p-phenylene] |
| 2 | ![benzimidazole with phenyl and methyl] | ![p-phenylene] |
| 3 | ![benzimidazole with phenyl and methyl] | ![p-phenylene] |
| 4 | ![benzimidazole with phenyl and methyl] | ![p-phenylene] |

-continued
| | HAr-L-Ar¹-Ar² | |
|---|---|---|
| 5 | 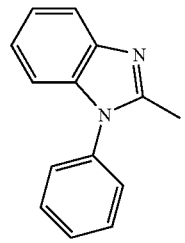 | 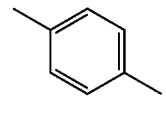 |
| 6 | 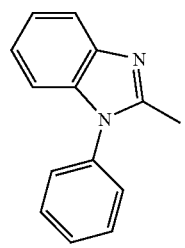 | 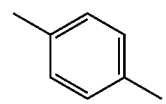 |
| 7 | 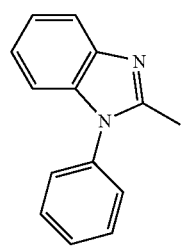 | 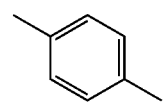 |
| 8 | 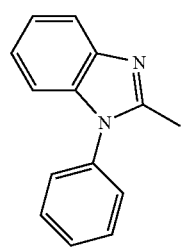 | 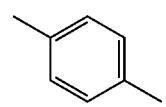 |
| 9 | 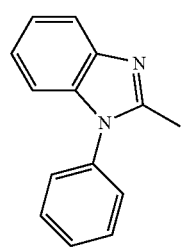 | 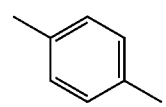 |
| 10 | 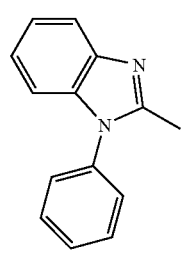 | 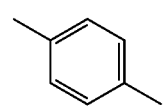 |

-continued
| | HAr-L-Ar¹-Ar² | |
|---|---|---|
| 11 | 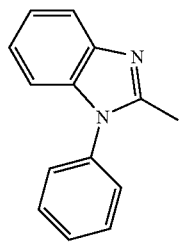 | 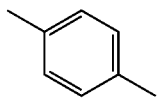 |
| 12 | 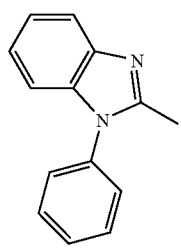 | 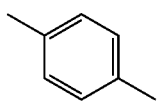 |
| 13 | 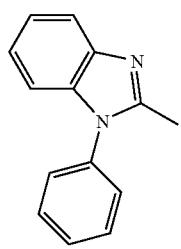 | 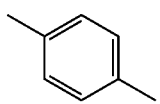 |
| 14 | 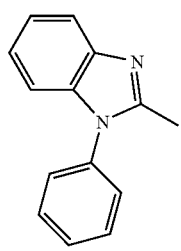 | 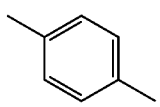 |
| 2-1 | 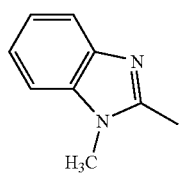 | 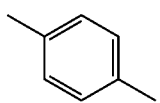 |
| 2 | 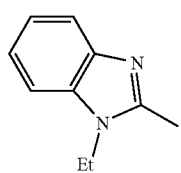 | 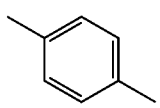 |
| 3 | 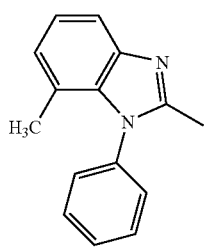 | 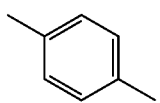 |

-continued
| | HAr-L-Ar¹-Ar² | |
|---|---|---|
| 4 | 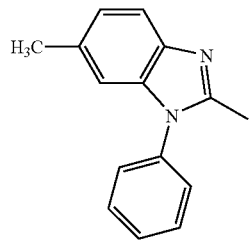 | 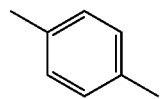 |
| 5 | 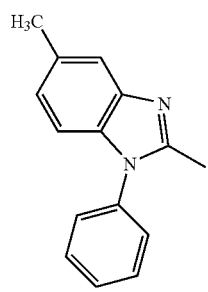 | 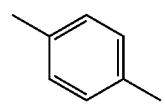 |
| 6 | 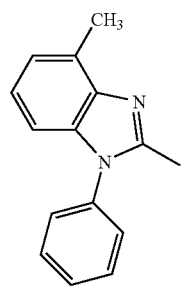 | 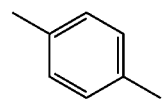 |
| 7 | 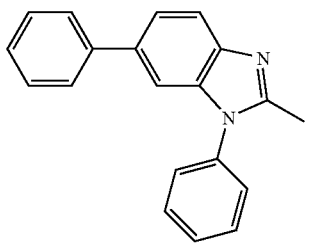 | 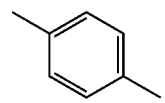 |
| 8 | 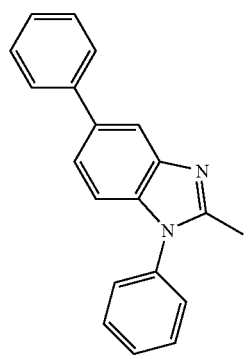 | 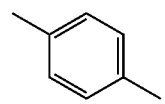 |

-continued
| | HAr-L-Ar¹-Ar² | |
|---|---|---|
| 9 | 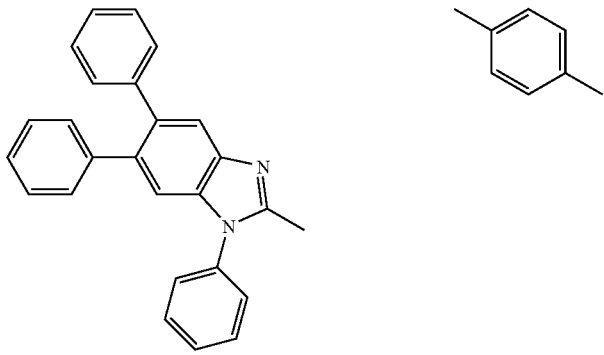 | |
| 3-1 | 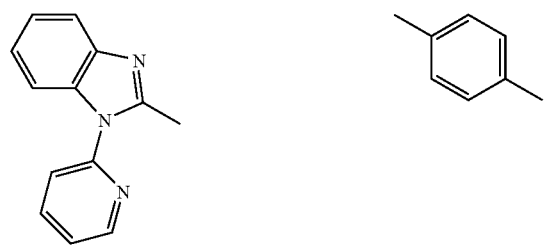 | |
| 2 | 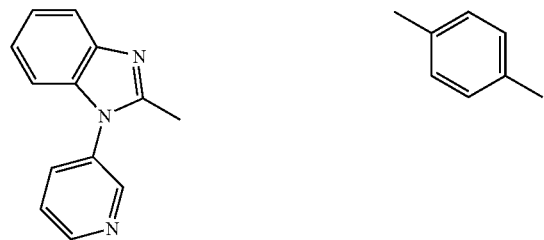 | |
| 3 | 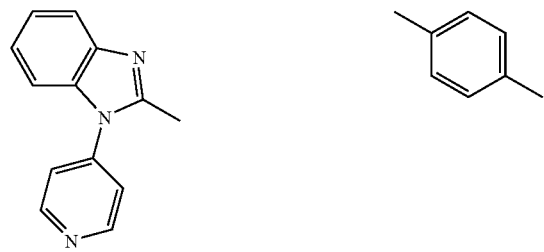 | |
| 4 | 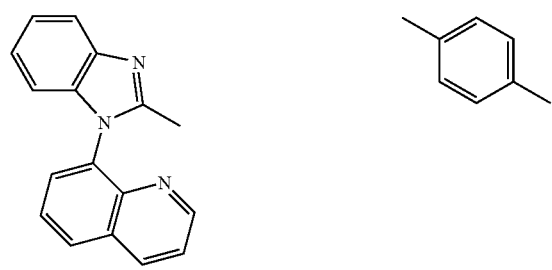 | |

-continued
| | HAr-L-Ar¹-Ar² | |
|---|---|---|
| 5 | 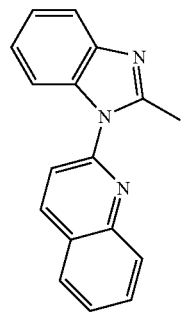 | 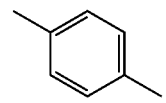 |
| 6 | 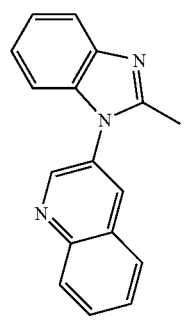 | 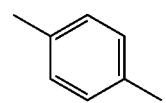 |
| 4-1 | 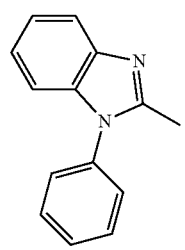 |  |
| 2 | 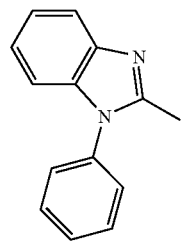 | 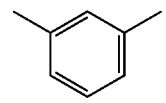 |
| 3 | 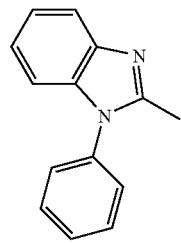 | 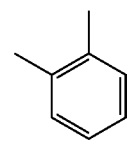 |

-continued
| | HAr-L-Ar¹-Ar² | |
|---|---|---|
| 4 | 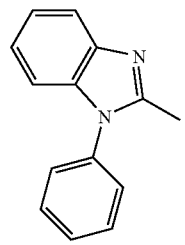 | 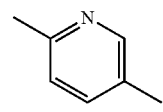 |
| 5 | 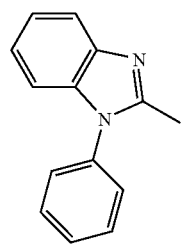 | 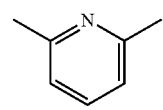 |
| 6 | 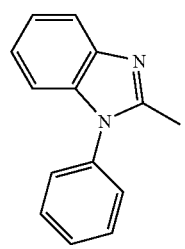 | 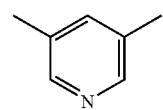 |
| 7 | 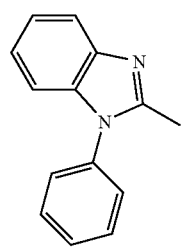 | 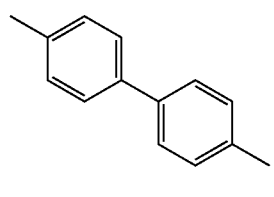 |
| 8 | 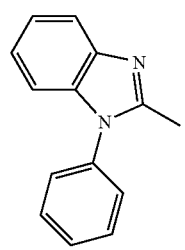 | 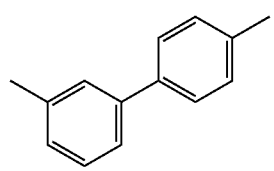 |
| 9 | 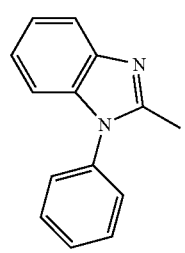 | 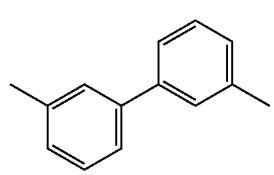 |

-continued
| | HAr-L-Ar¹-Ar² | |
|---|---|---|
| 10 | 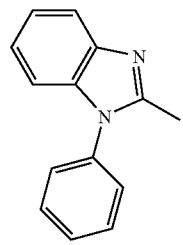 | 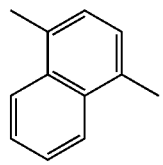 |
| 11 | 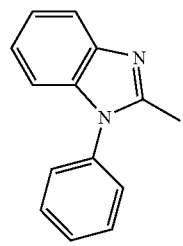 | 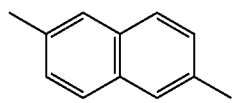 |
| 12 | 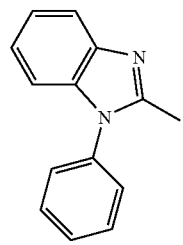 | 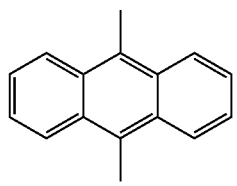 |
| 5-1 | 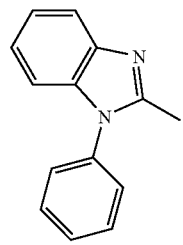 | 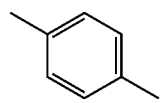 |
| 2 | 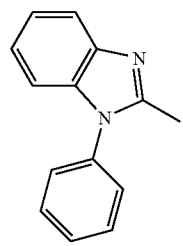 | 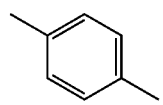 |
| 3 | 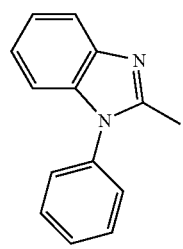 | 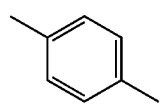 |

-continued
| | HAr-L-Ar¹-Ar² | |
|---|---|---|
| 4 | 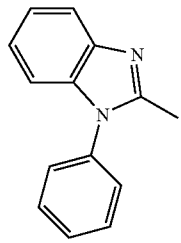 | 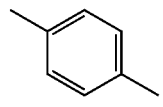 |
| 5 | 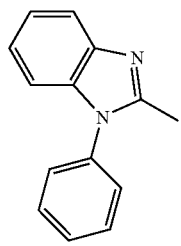 | 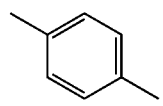 |
| 6 | 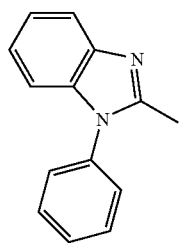 | 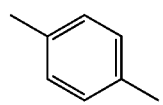 |
| 6-1 | 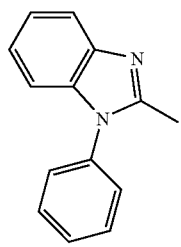 | 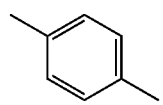 |
| 2 | 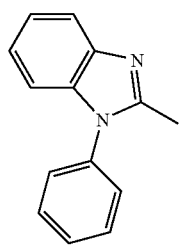 | 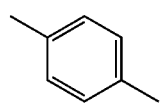 |
| 3 | 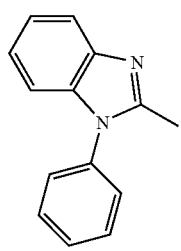 | 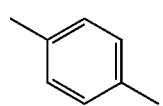 |

-continued
| | HAr-L-Ar¹-Ar² | |
|---|---|---|
| 4 | 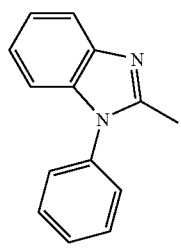 | 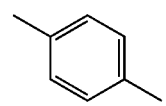 |
| 5 | 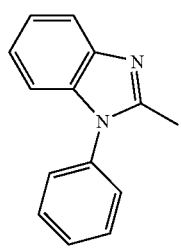 | 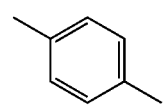 |
| 7-1 | 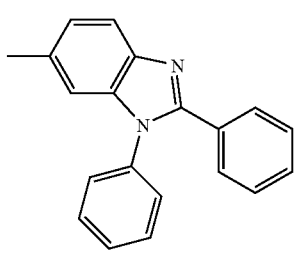 | 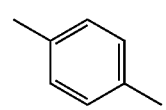 |
| 2 | 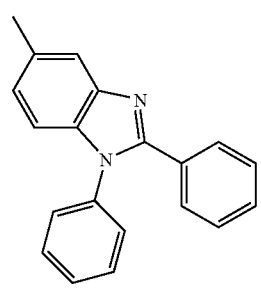 | 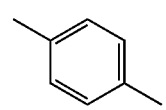 |
| 3 | 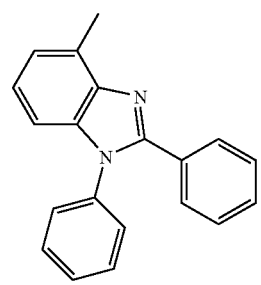 | 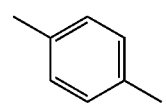 |
| 4 | 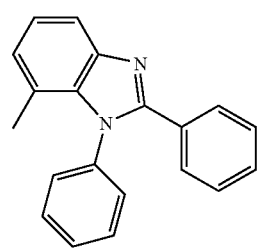 | 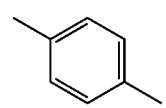 |

-continued
| | HAr-L-Ar¹-Ar² | |
|---|---|---|
| 5 | 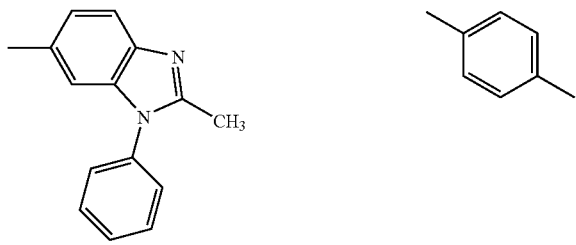 | 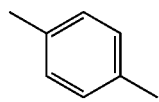 |
| 6 | 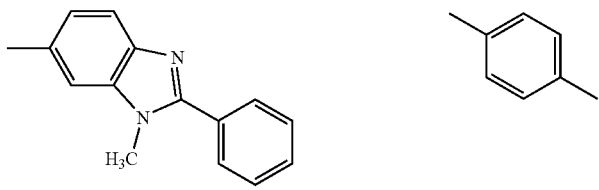 | 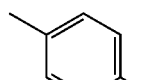 |
| 7 | 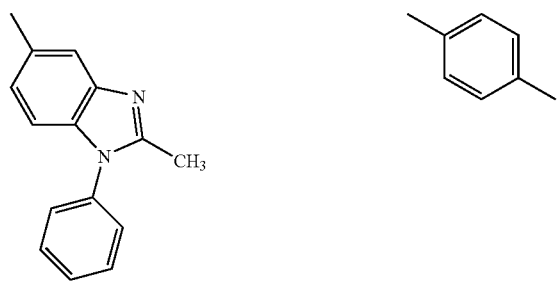 | 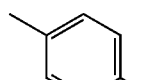 |
| 8 | 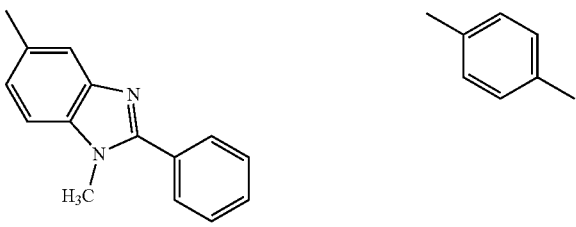 | 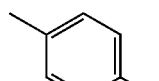 |
| 9 | 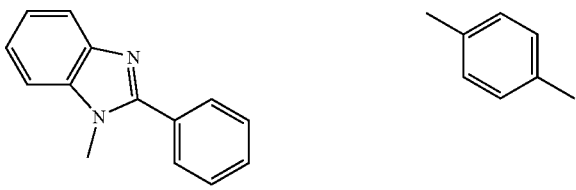 | 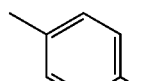 |
| 10 |  | 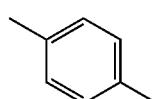 |
| 8-1 | 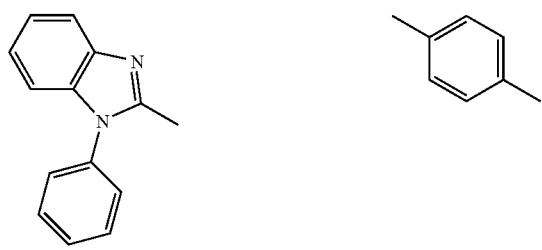 | 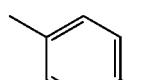 |

-continued
| | HAr-L-Ar¹-Ar² | |
|---|---|---|
| 2 | 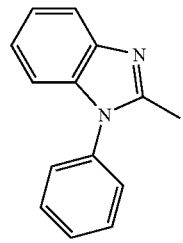 | 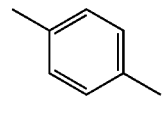 |
| 3 | 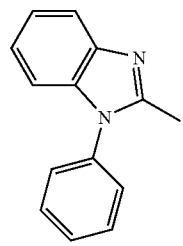 | 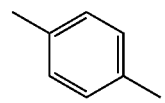 |
| 4 | 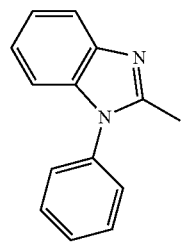 | 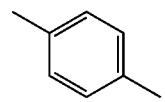 |
| 5 | 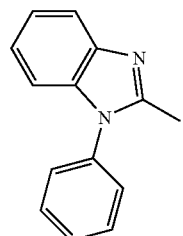 | 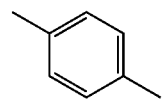 |
| 6 | 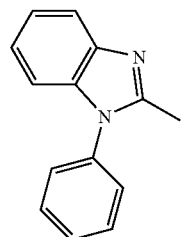 | 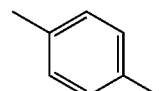 |
| 7 | 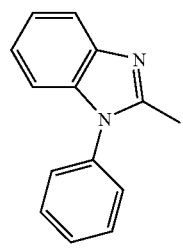 | 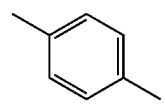 |

-continued
| | HAr-L-Ar¹-Ar² | |
|---|---|---|
| 8 | 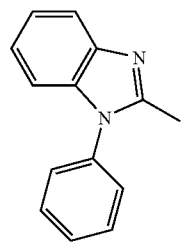 | 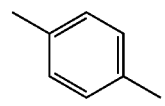 |
| 9 | 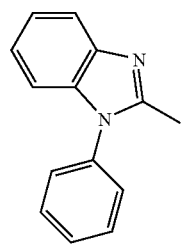 | 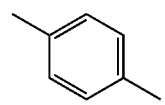 |
| 10 | 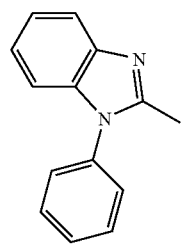 | 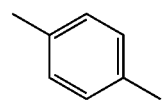 |
| 11 | 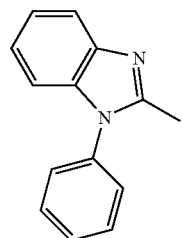 | 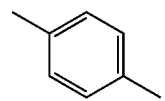 |
| 12 | 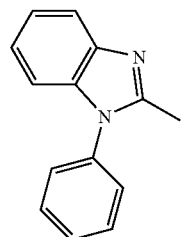 | 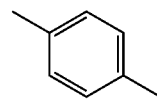 |
| 13 | 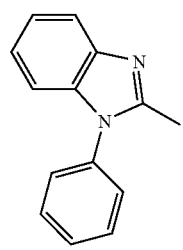 | 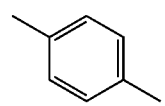 |

-continued
| | HAr-L-Ar¹-Ar² | |
|---|---|---|
| 9-1 | 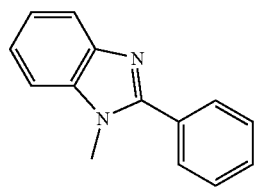 | 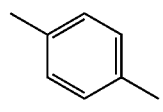 |
| 2 | 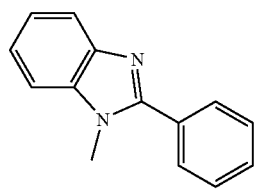 | 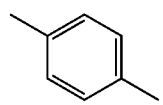 |
| 3 | 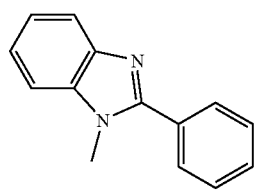 | 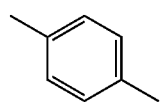 |
| 4 | 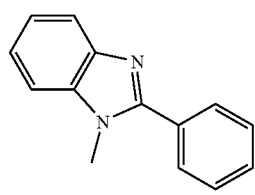 | 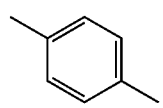 |
| 5 | 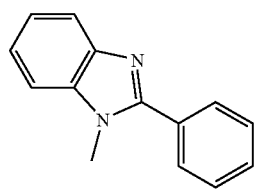 | 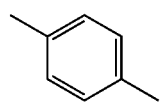 |
| 6 | 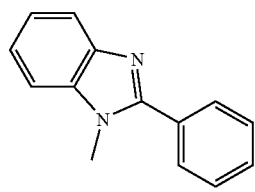 | 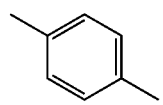 |
| 7 | 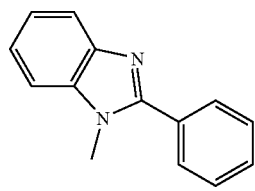 | 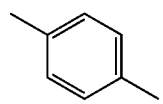 |
| 8 | 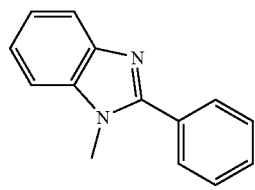 | 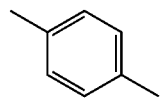 |

-continued
| | HAr-L-Ar¹-Ar² | |
|---|---|---|
| 9 | 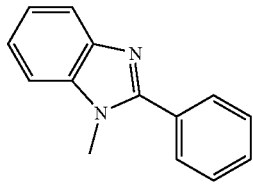 | 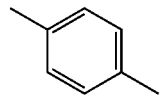 |
| 10 | 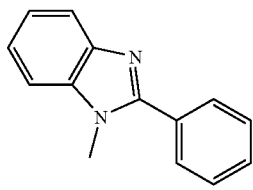 | 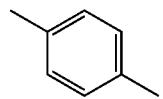 |
| 11 | 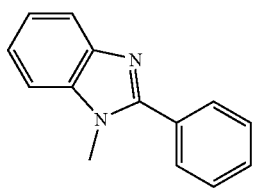 | 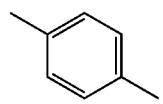 |
| 12 | 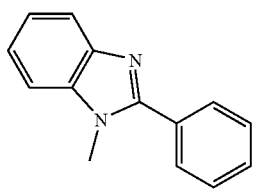 | 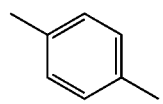 |
| 13 | 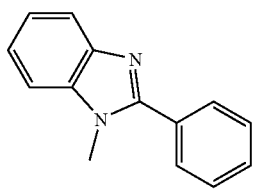 | 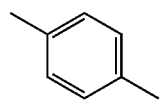 |
| 14 | 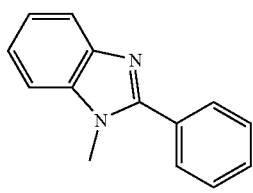 | 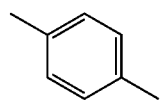 |
| 10-1 | 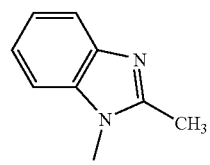 | 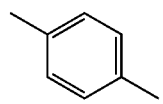 |
| 2 | 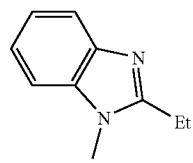 | 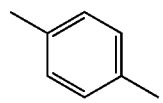 |

-continued
| | HAr-L-Ar¹-Ar² | |
|---|---|---|
| 3 | 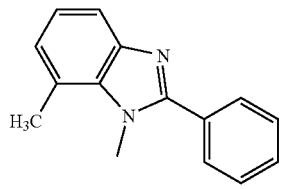 | 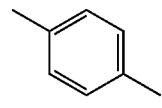 |
| 4 | 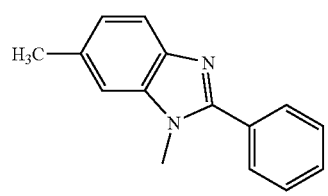 | 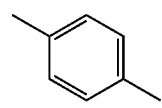 |
| 5 | 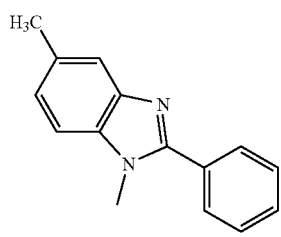 | 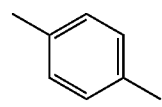 |
| 6 | 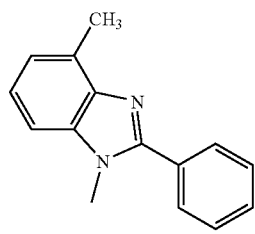 | 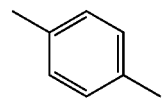 |
| 7 | 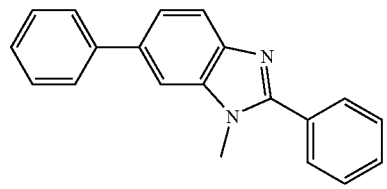 | 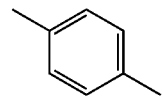 |
| 8 | 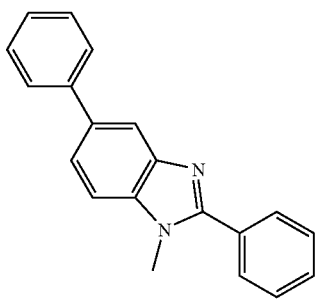 | 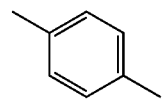 |

-continued
| | HAr-L-Ar¹-Ar² | |
|---|---|---|
| 9 | 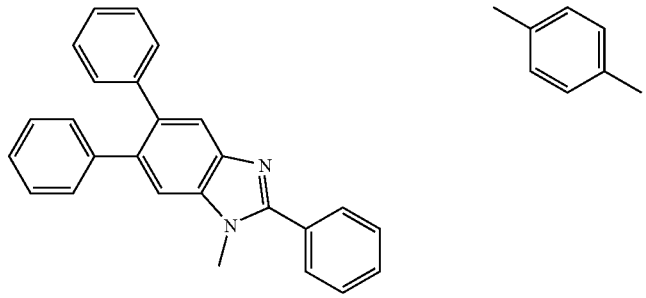 | |
| 11-1 | 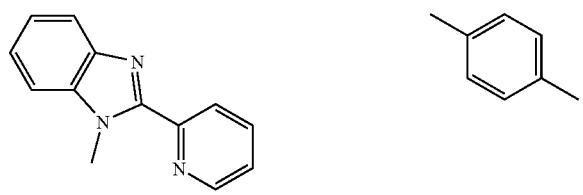 | |
| 2 | 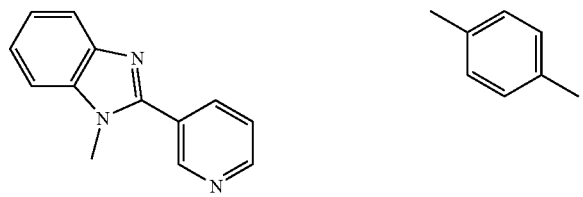 | |
| 3 | 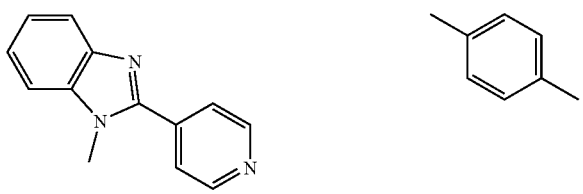 | |
| 4 | 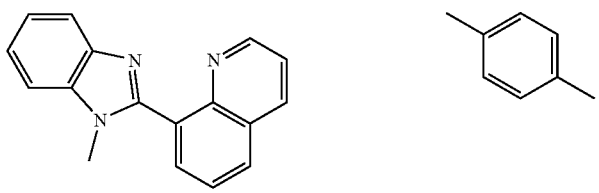 | |
| 5 | 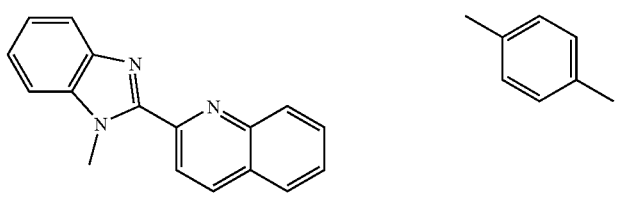 | |
| 6 | 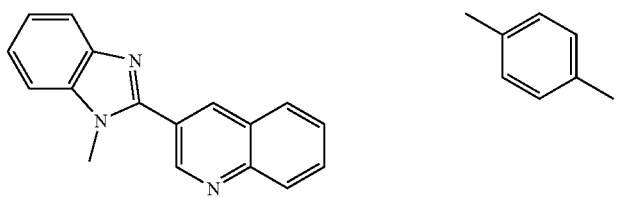 | |

-continued
| | HAr-L-Ar¹-Ar² | |
|---|---|---|
| 12-1 | 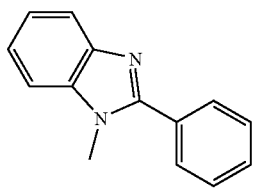 |  |
| 2 | 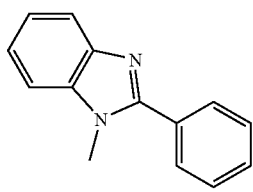 | 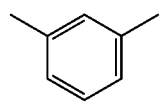 |
| 3 | 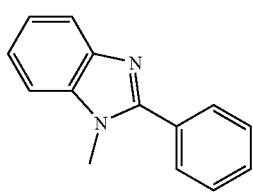 | 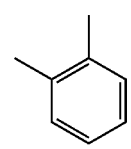 |
| 4 | 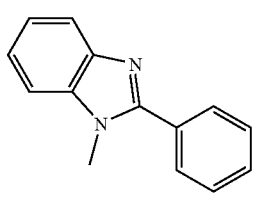 | 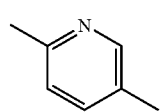 |
| 5 | 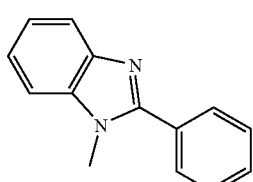 | 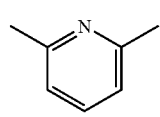 |
| 6 | 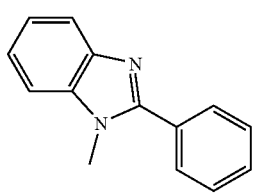 | 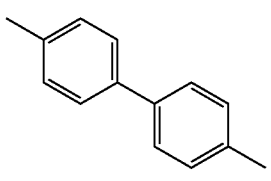 |
| 7 | 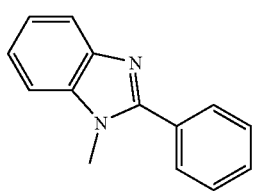 | 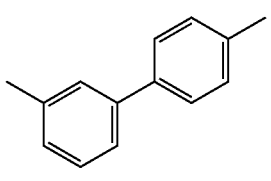 |
| 8 | 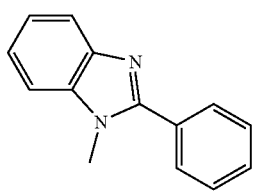 | 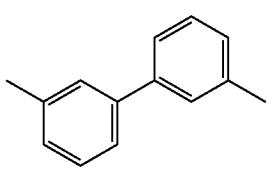 |

-continued
| | HAr-L-Ar¹-Ar² | |
|---|---|---|
| 9 | 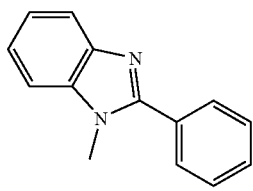 | 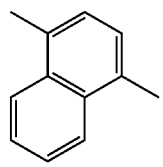 |
| 10 | 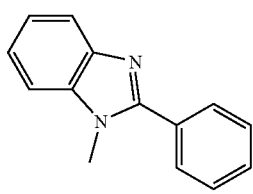 | 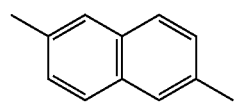 |
| 11 | 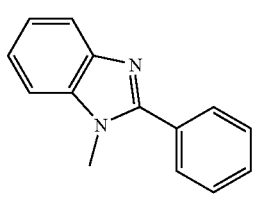 | 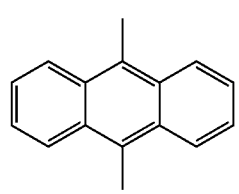 |
| 13-1 | 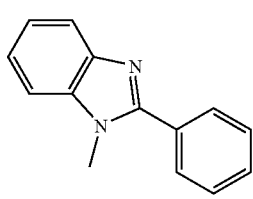 | 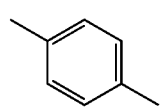 |
| 2 | 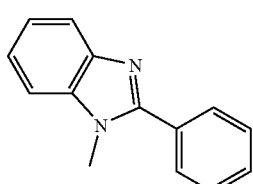 | 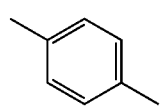 |
| 3 | 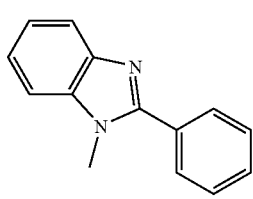 | 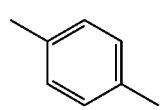 |
| 4 | 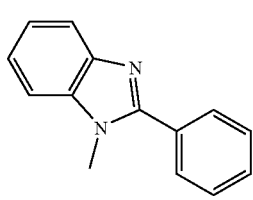 | 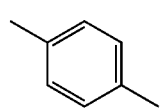 |
| 5 | 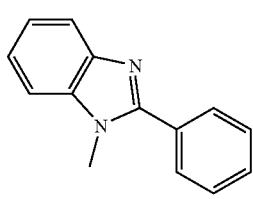 | 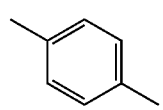 |

-continued
| | HAr-L-Ar¹-Ar² | |
|---|---|---|
| 6 | 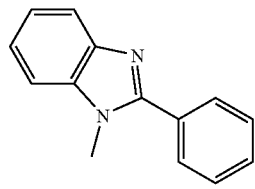 | 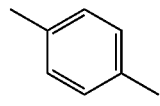 |
| 14-1 | 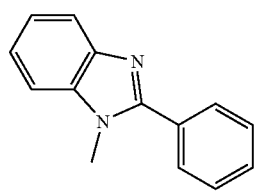 | 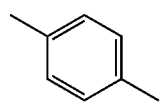 |
| 2 | 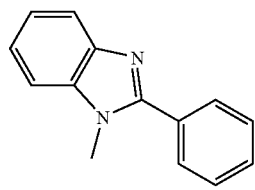 | 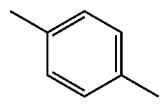 |
| 3 | 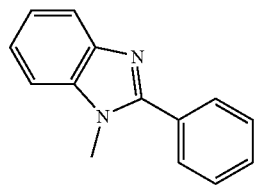 | 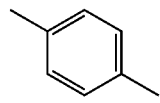 |
| 4 | 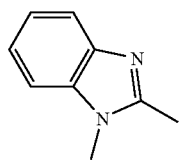 | 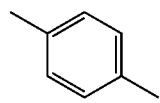 |
| 5 | 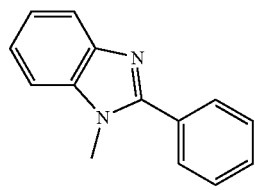 | 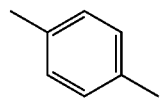 |
| 15-1 | 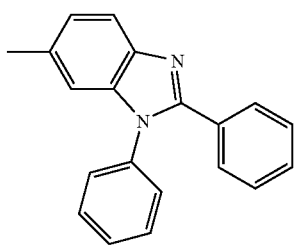 |  |

| HAr-L-Ar¹-Ar² |
| --- |
| 2 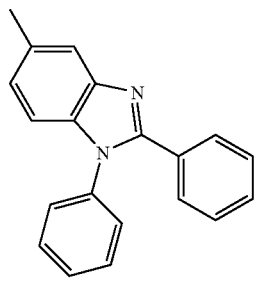 \ |
| 3 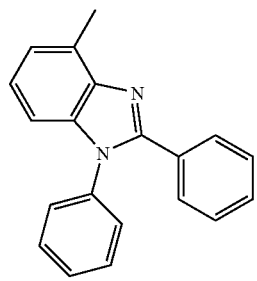 \ |
| 4 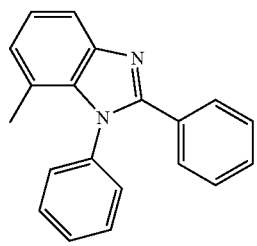 \ |
| 5 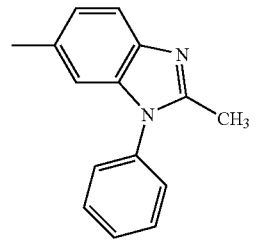 \ |
| 6 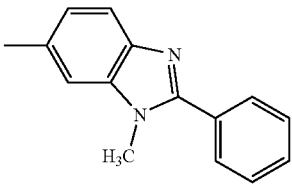 \ |
| 7 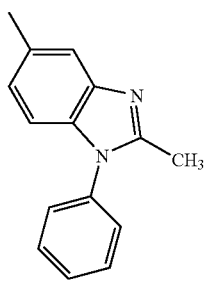 \ |

-continued
| | HAr-L-Ar¹-Ar² | |
|---|---|---|
| 8 | 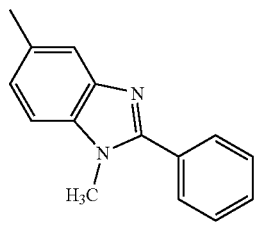 | \ |
| 9 | 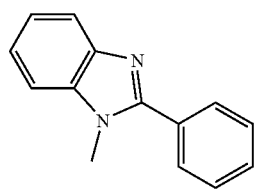 | \ |
| 10 | 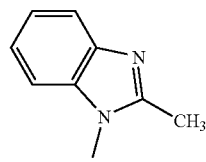 | \ |
| 16-1 | 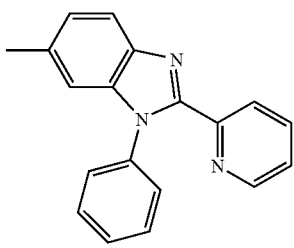 | \ |
| 2 | 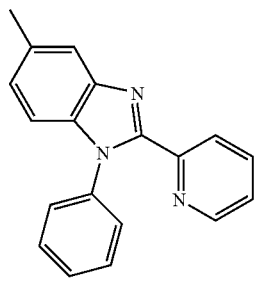 | \ |
| 3 | 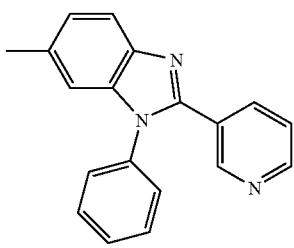 | \ |

-continued
| | HAr-L-Ar¹-Ar² | |
|---|---|---|
| 4 | 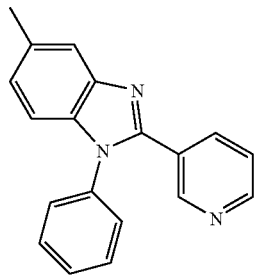 | ─ |
| 5 | 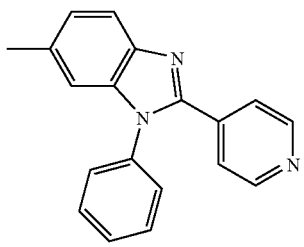 | ─ |
| 6 | 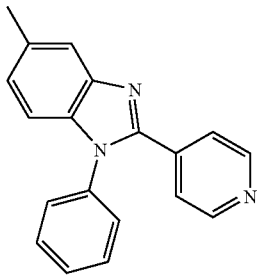 | ─ |
| 7 | 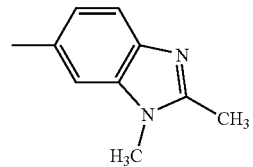 | ─ |
| 8 | 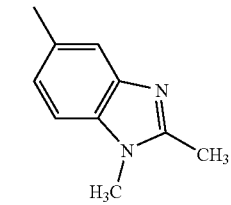 | ─ |
| 17-1 | 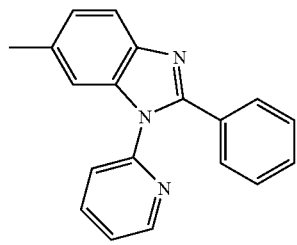 | ─ |

-continued
| | HAr-L-Ar¹-Ar² | |
|---|---|---|
| 2 | 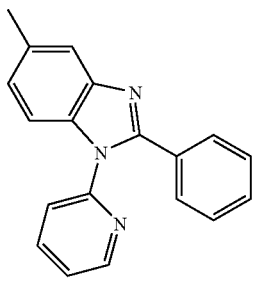 | — |
| 3 | 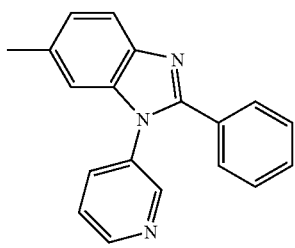 | — |
| 4 | 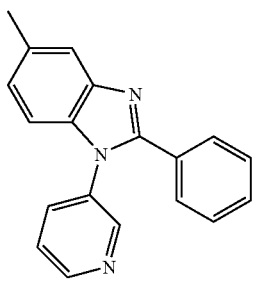 | — |
| 5 | 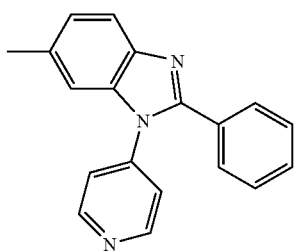 | — |
| 6 | 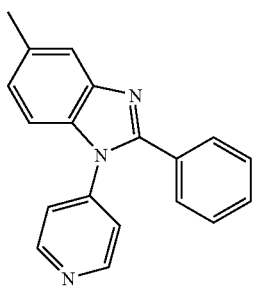 | — |

-continued
| | HAr-L-Ar¹-Ar² | |
|---|---|---|
| 7 | 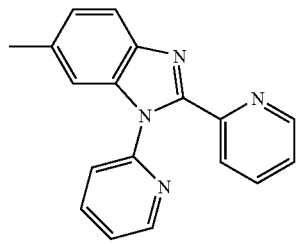 | — |
| 8 | 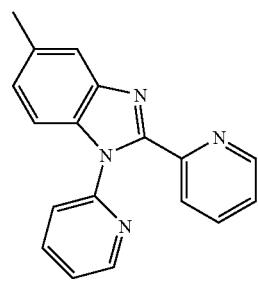 | — |
| | Ar¹ | Ar² |
|---|---|---|
| 1-1 | 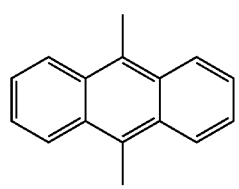 | 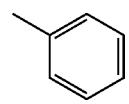 |
| 2 | 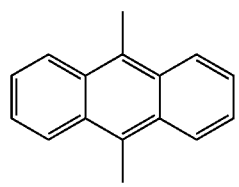 | 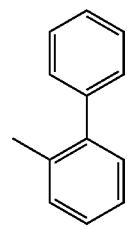 |
| 3 | 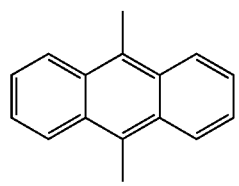 | 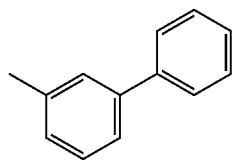 |
| 4 | 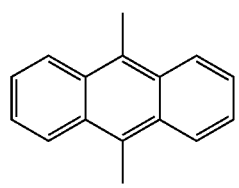 | 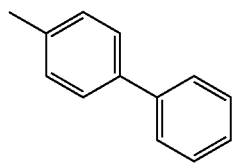 |

-continued
HAr-L-Ar¹-Ar²
| | | |
|---|---|---|
| 5 | 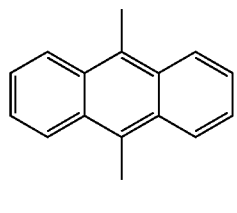 | 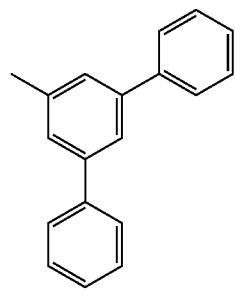 |
| 6 | 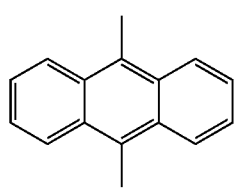 | 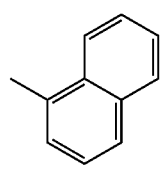 |
| 7 | 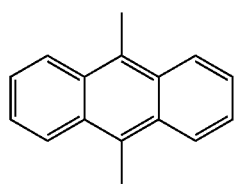 | 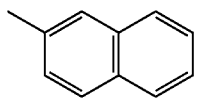 |
| 8 | 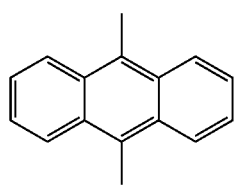 | 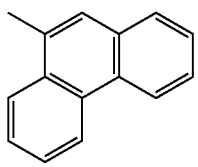 |
| 9 | 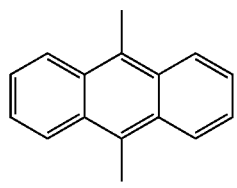 | 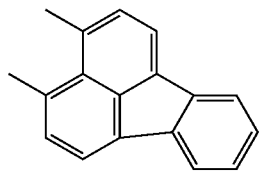 |
| 10 | 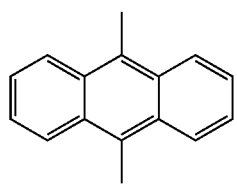 | 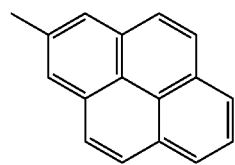 |
| 11 | 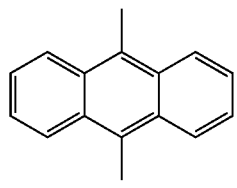 | 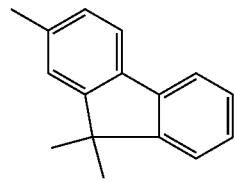 |

-continued
| | HAr-L-Ar¹-Ar² | |
|---|---|---|
| 12 | 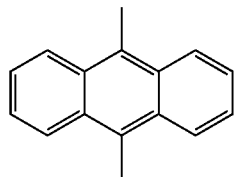 | 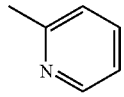 |
| 13 | 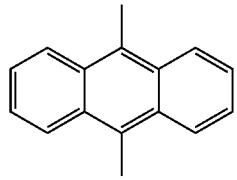 | 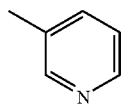 |
| 14 | 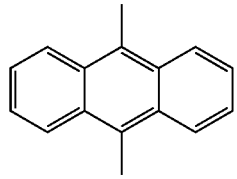 | 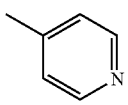 |
| 2-1 | 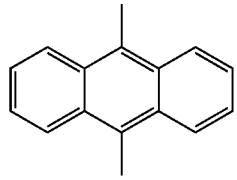 | 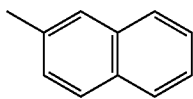 |
| 2 | 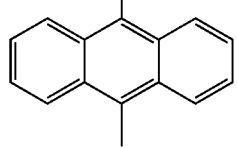 | 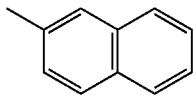 |
| 3 | 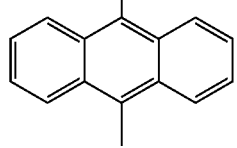 | 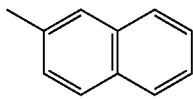 |
| 4 | 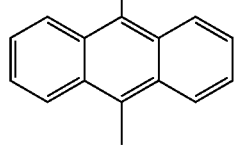 | 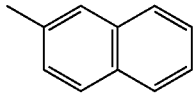 |
| 5 | 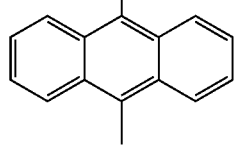 | 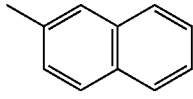 |

-continued
| | HAr-L-Ar¹-Ar² | |
|---|---|---|
| 6 | 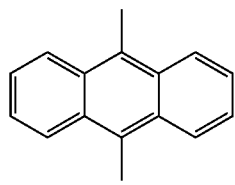 | 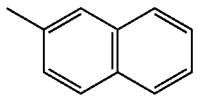 |
| 7 | 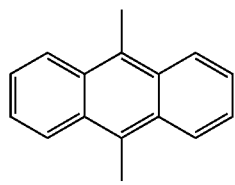 | 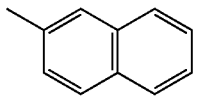 |
| 8 | 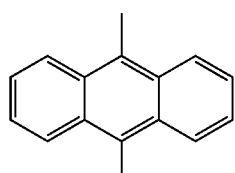 | 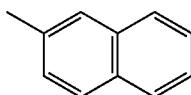 |
| 9 | 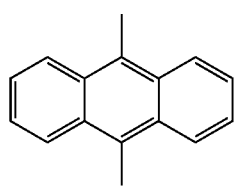 | 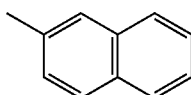 |
| 3-1 | 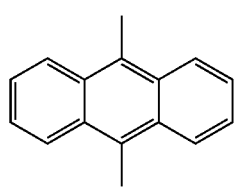 | 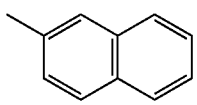 |
| 2 | 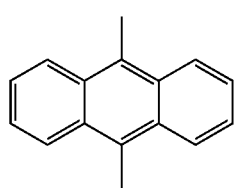 | 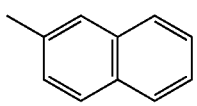 |
| 3 | 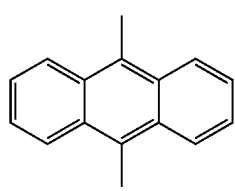 | 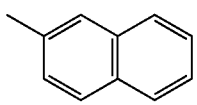 |
| 4 | 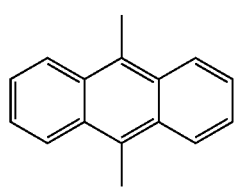 | 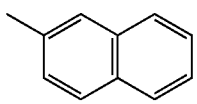 |

-continued
| | HAr-L-Ar¹-Ar² | |
|---|---|---|
| 5 | 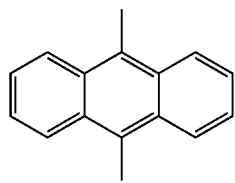 | 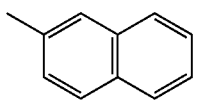 |
| 6 | 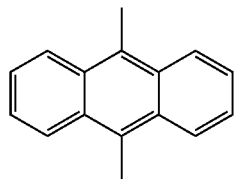 | 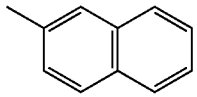 |
| 4-1 | 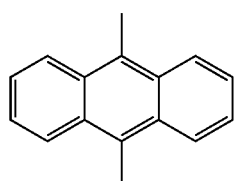 | 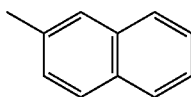 |
| 2 | 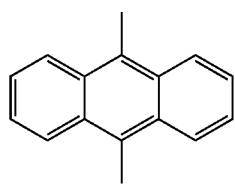 | 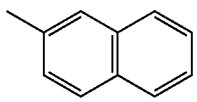 |
| 3 | 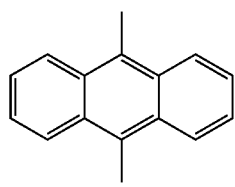 | 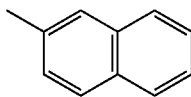 |
| 4 | 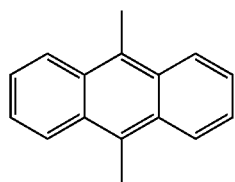 | 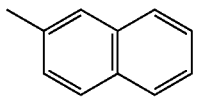 |
| 5 | 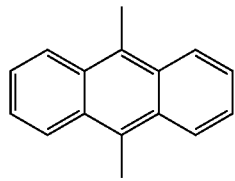 | 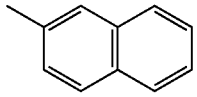 |
| 6 | 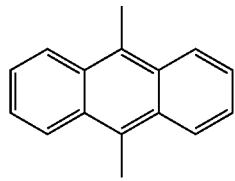 | 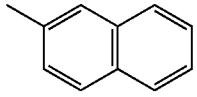 |

-continued
| | HAr-L-Ar¹-Ar² | |
|---|---|---|
| 7 | 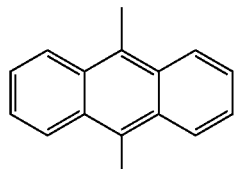 | 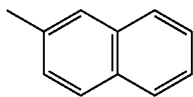 |
| 8 | 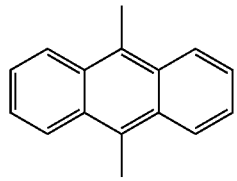 | 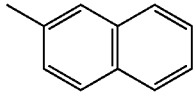 |
| 9 | 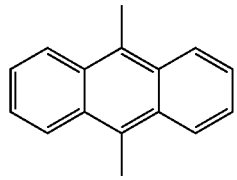 | 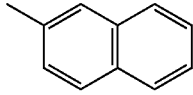 |
| 10 | 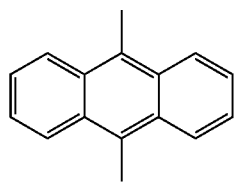 | 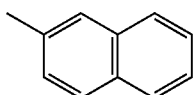 |
| 11 | 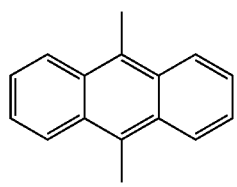 | 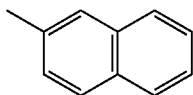 |
| 12 | 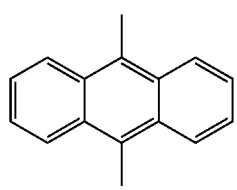 | 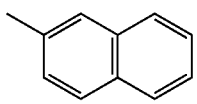 |
| 5-1 | 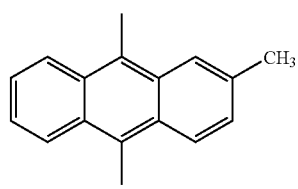 | 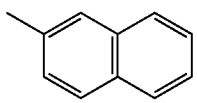 |
| 2 | 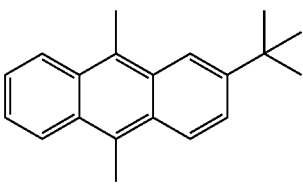 | 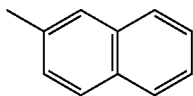 |

-continued
| | HAr-L-Ar¹-Ar² | |
|---|---|---|
| 3 | 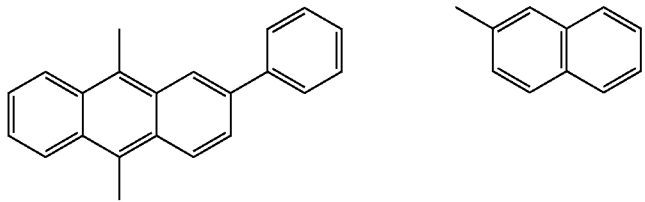 | |
| 4 | 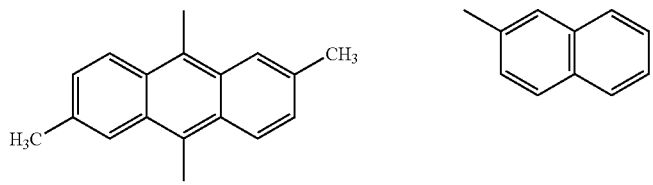 | |
| 5 | 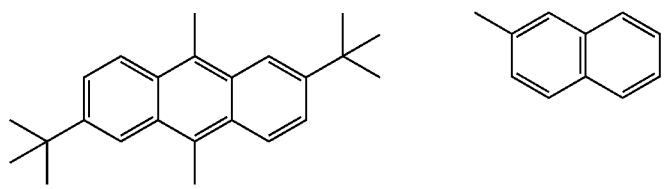 | |
| 6 | 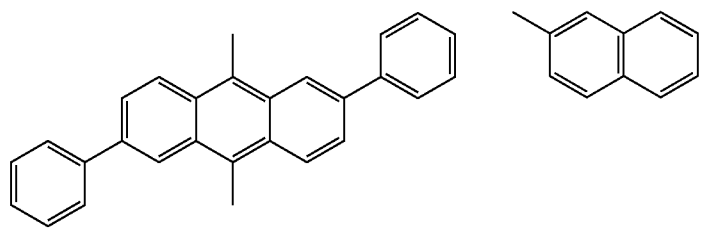 | |
| 6-1 | 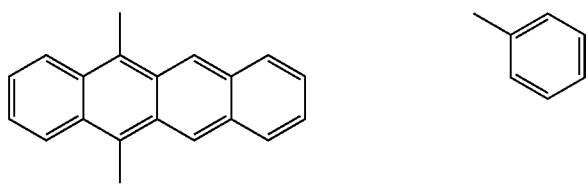 | |
| 2 | 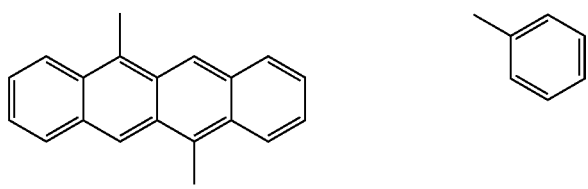 | |
| 3 | 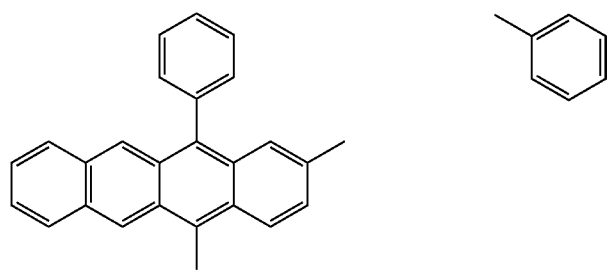 | |

-continued
| | HAr-L-Ar¹-Ar² | |
|---|---|---|
| 4 | 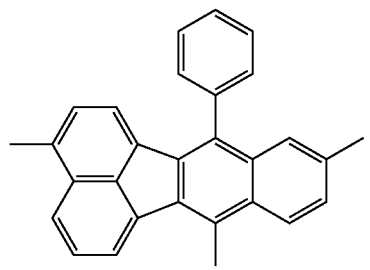 | 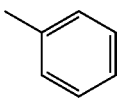 |
| 5 | 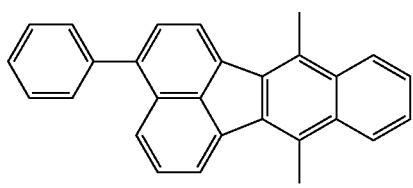 | 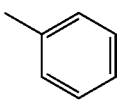 |
| 7-1 | 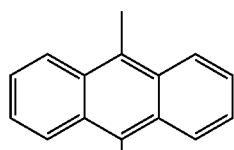 | 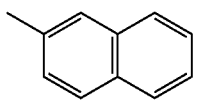 |
| 2 | 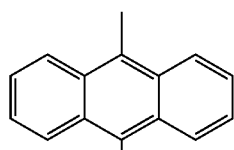 | 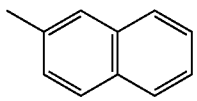 |
| 3 | 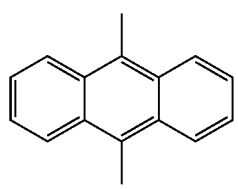 | 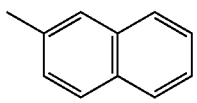 |
| 4 | 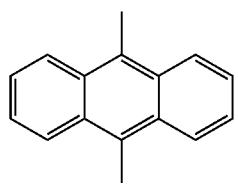 | 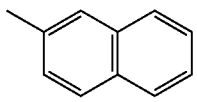 |
| 5 | 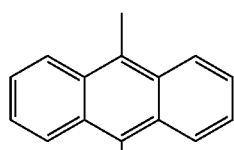 | 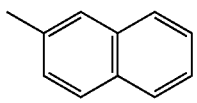 |
| 6 | 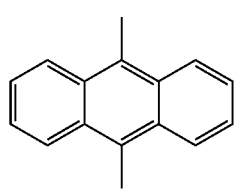 | 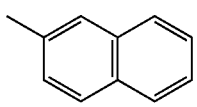 |

-continued
| | HAr-L-Ar¹-Ar² | |
|---|---|---|
| 7 | 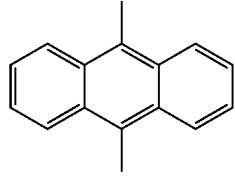 | 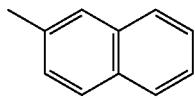 |
| 8 | 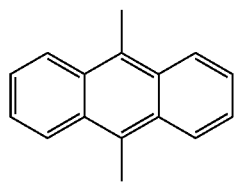 | 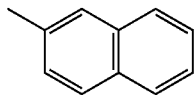 |
| 9 | 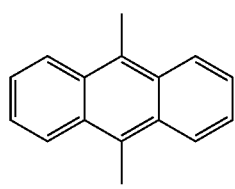 | 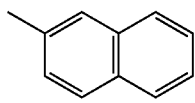 |
| 10 | 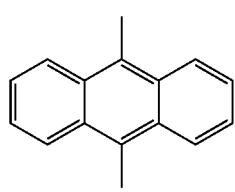 | 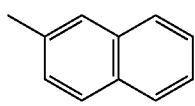 |
| 8-1 | 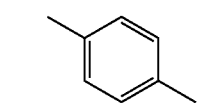 | 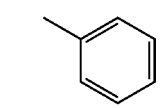 |
| 2 | 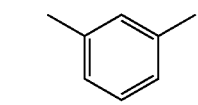 | 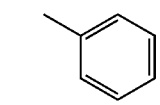 |
| 3 | 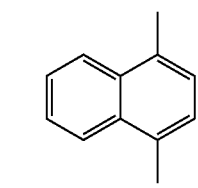 | 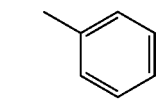 |
| 4 | 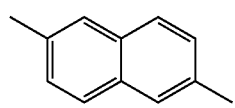 | 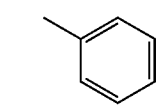 |
| 5 | 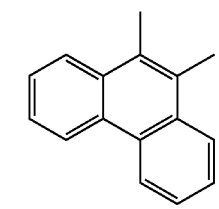 | 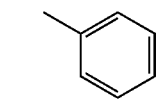 |

| | HAr-L-Ar¹-Ar² | |
|---|---|---|
| 6 | 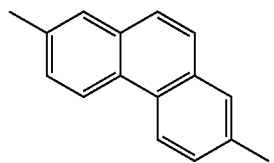 | 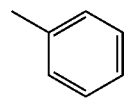 |
| 7 | 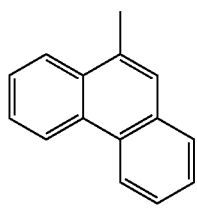 |  |
| 8 | 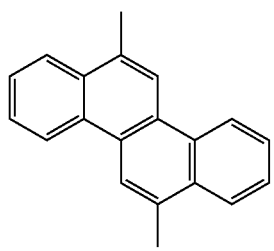 | 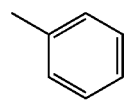 |
| 9 | 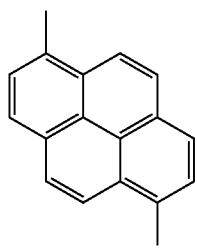 | 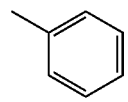 |
| 10 | 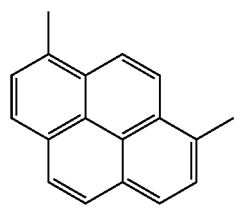 | 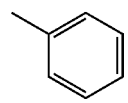 |
| 11 | 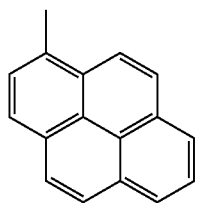 |  |
| 12 | 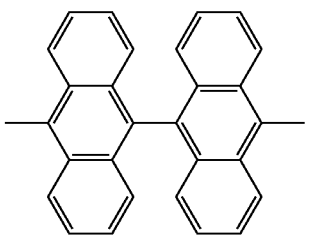 | 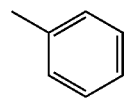 |

-continued
| | HAr-L-Ar¹-Ar² | |
|---|---|---|
| 13 | 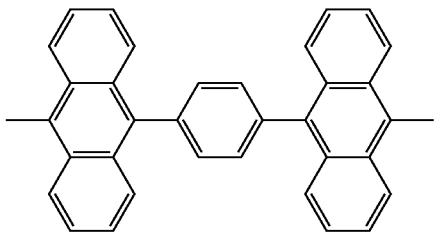 | 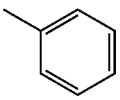 |
| 9-1 | 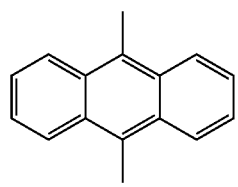 | 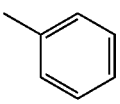 |
| 2 | 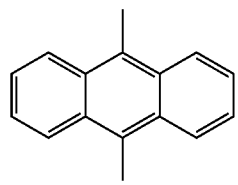 | 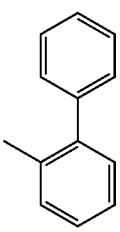 |
| 3 | 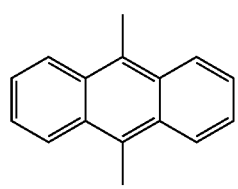 | 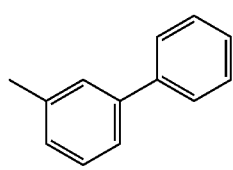 |
| 4 | 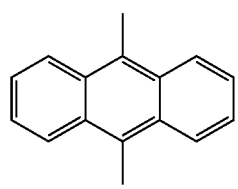 | 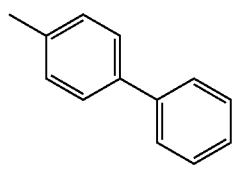 |
| 5 | 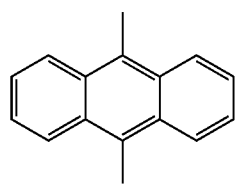 | 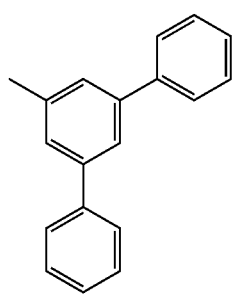 |
| 6 | 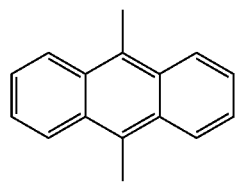 | 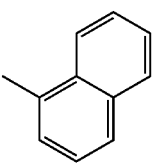 |

| HAr-L-Ar¹-Ar² | |
|---|---|
| 7 | 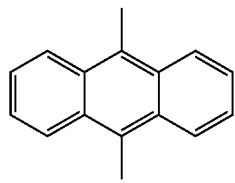 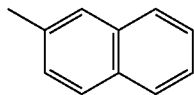 |
| 8 | 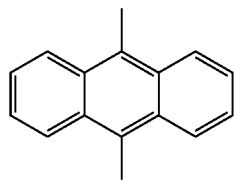 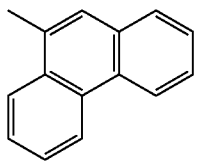 |
| 9 | 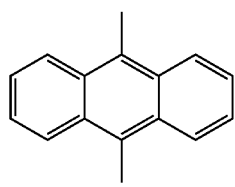 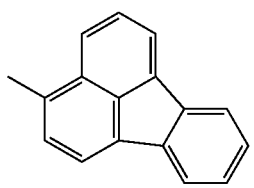 |
| 10 | 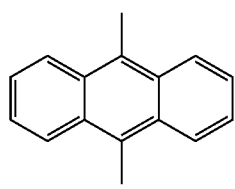 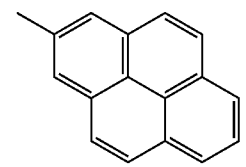 |
| 11 | 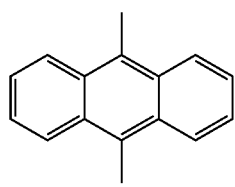 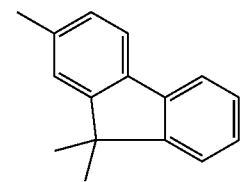 |
| 12 | 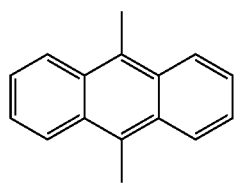 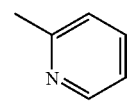 |
| 13 | 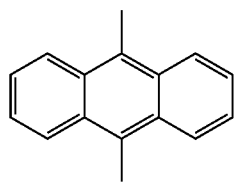 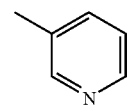 |
| 14 | 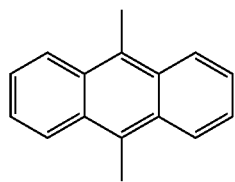 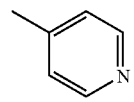 |

-continued
| | HAr-L-Ar¹-Ar² | |
|---|---|---|
| 10-1 | 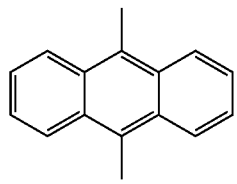 | 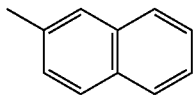 |
| 2 | 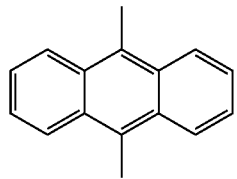 | 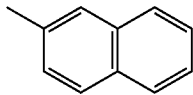 |
| 3 | 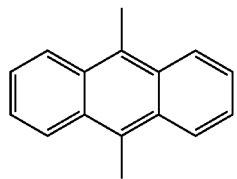 | 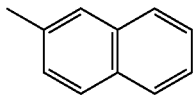 |
| 4 | 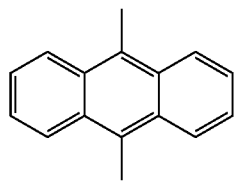 | 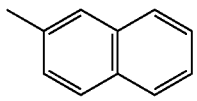 |
| 5 | 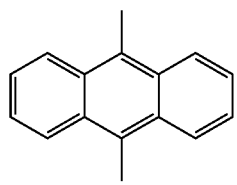 | 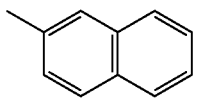 |
| 6 | 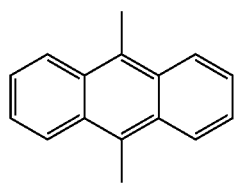 | 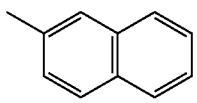 |
| 7 | 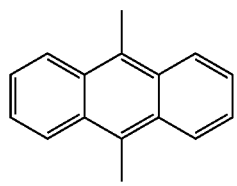 | 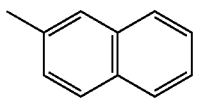 |
| 8 | 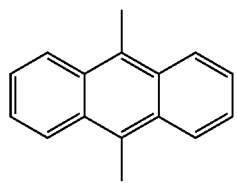 | 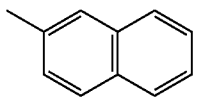 |

-continued
| | HAr-L-Ar¹-Ar² | |
|---|---|---|
| 9 | 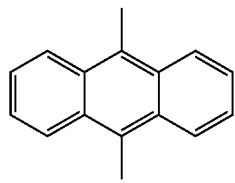 | 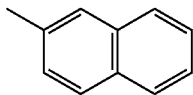 |
| 11-1 | 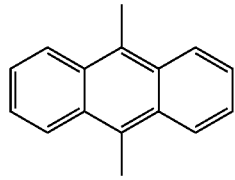 | 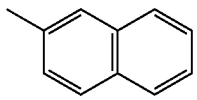 |
| 2 | 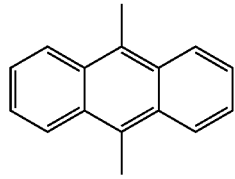 | 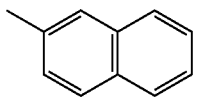 |
| 3 | 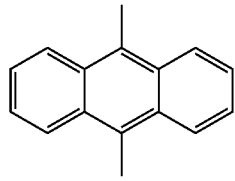 | 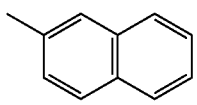 |
| 4 | 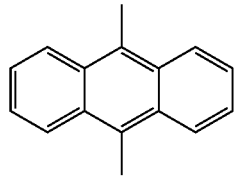 | 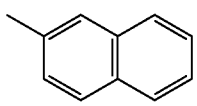 |
| 5 | 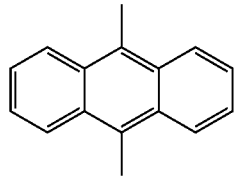 | 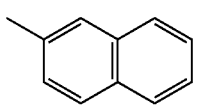 |
| 6 | 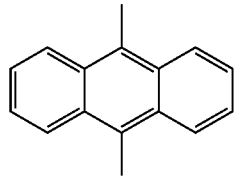 | 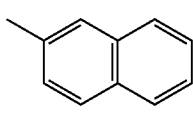 |
| 12-1 | 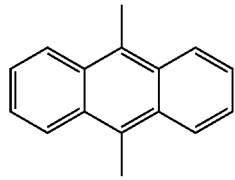 | 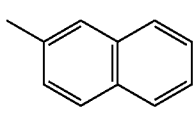 |

-continued
| | HAr-L-Ar¹-Ar² | |
|---|---|---|
| 2 | 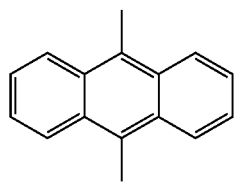 | 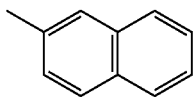 |
| 3 | 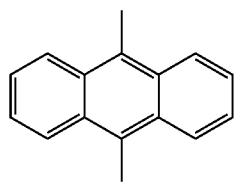 | 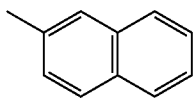 |
| 4 | 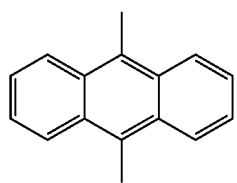 | 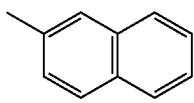 |
| 5 | 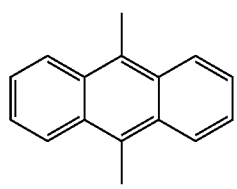 | 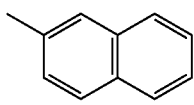 |
| 6 | 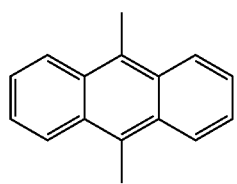 | 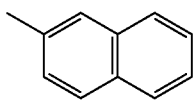 |
| 7 | 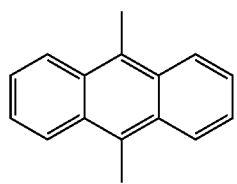 | 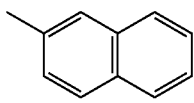 |
| 8 | 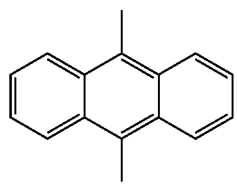 | 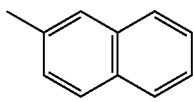 |
| 9 | 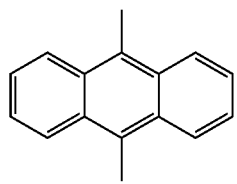 | 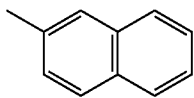 |

| | -continued | |
|---|---|---|
| | HAr-L-Ar¹-Ar² | |
| 10 | 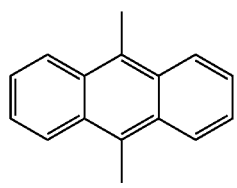 | 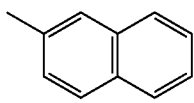 |
| 11 | 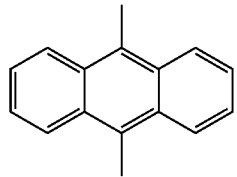 | 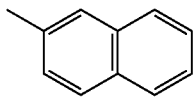 |
| 13-1 | 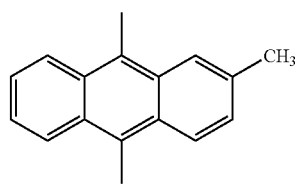 | 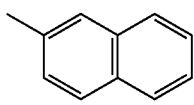 |
| 2 | 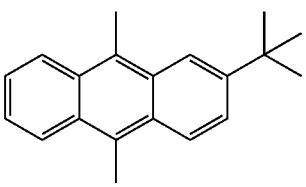 | 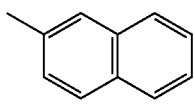 |
| 3 | 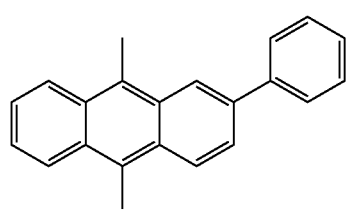 | 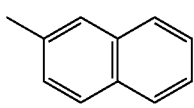 |
| 4 | 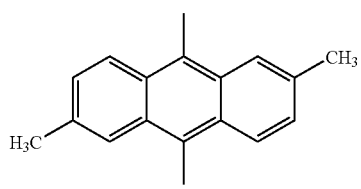 | 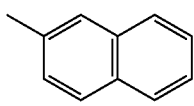 |
| 5 | 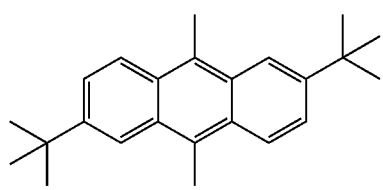 | 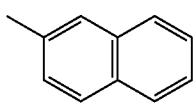 |
| 6 | 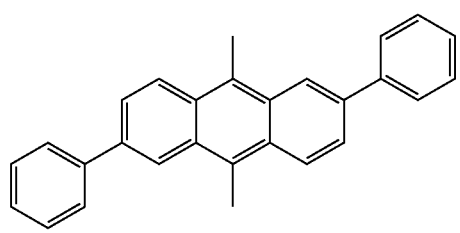 | 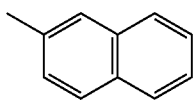 |

-continued
| HAr-L-Ar¹-Ar² | | |
|---|---|---|
| 14-1 | 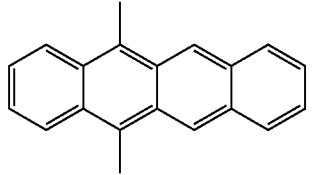 | 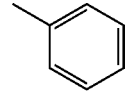 |
| 2 | 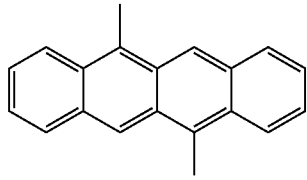 | 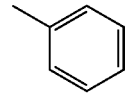 |
| 3 | 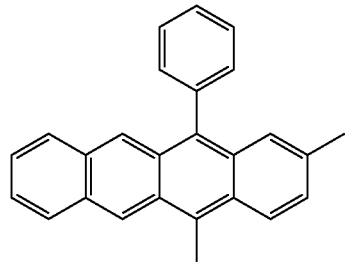 | 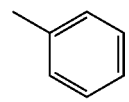 |
| 4 | 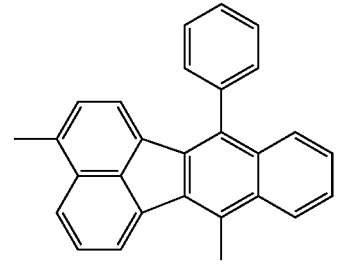 | 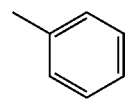 |
| 5 | 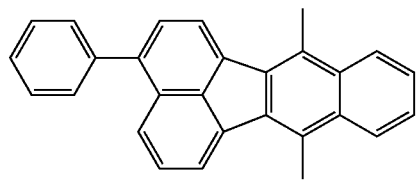 | 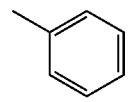 |
| 15-1 | 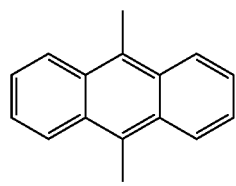 | 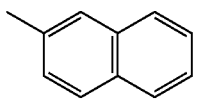 |
| 2 | 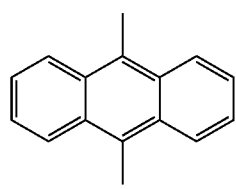 | 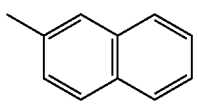 |

-continued
| | HAr-L-Ar¹-Ar² | |
|---|---|---|
| 3 | 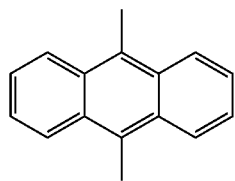 | 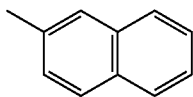 |
| 4 | 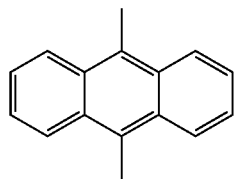 | 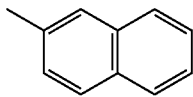 |
| 5 | 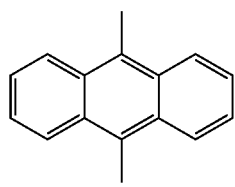 | 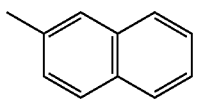 |
| 6 | 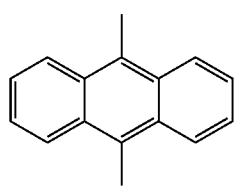 | 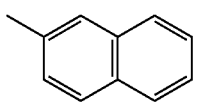 |
| 7 | 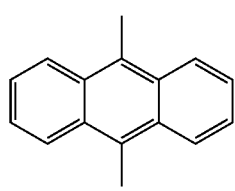 | 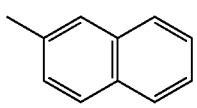 |
| 8 | 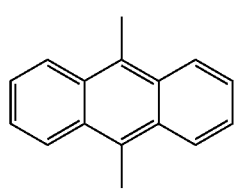 | 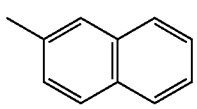 |
| 9 | 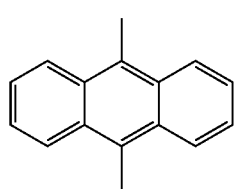 | 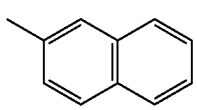 |
| 10 | 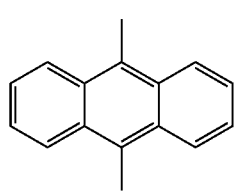 | 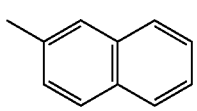 |

-continued
| | HAr-L-Ar¹-Ar² | |
|---|---|---|
| 16-1 | 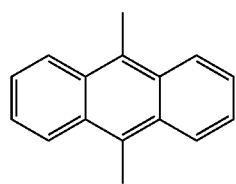 | 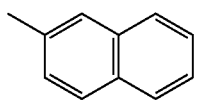 |
| 2 | 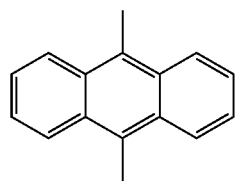 | 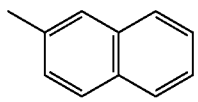 |
| 3 | 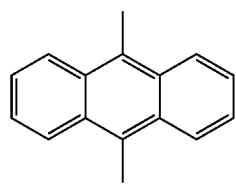 | 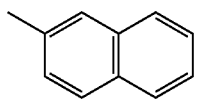 |
| 4 | 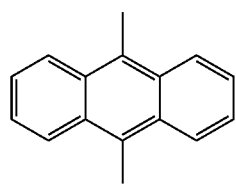 | 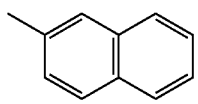 |
| 5 | 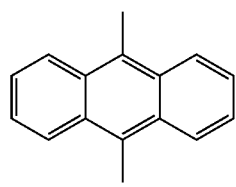 | 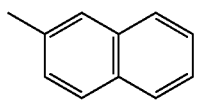 |
| 6 | 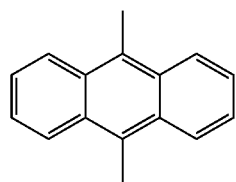 | 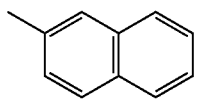 |
| 7 | 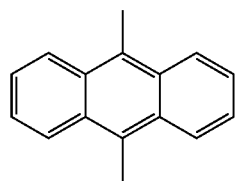 | 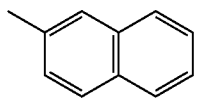 |
| 8 | 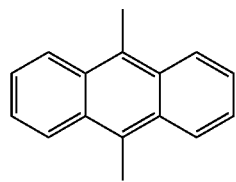 | 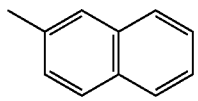 |

-continued
| | HAr-L-Ar¹-Ar² | |
|---|---|---|
| 17-1 | 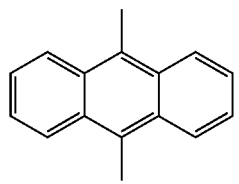 | 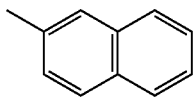 |
| 2 | 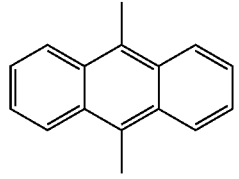 | 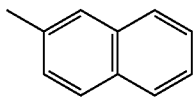 |
| 3 | 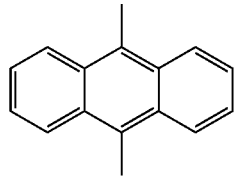 | 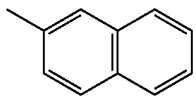 |
| 4 | 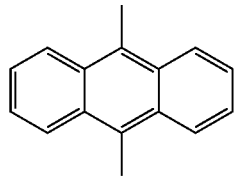 | 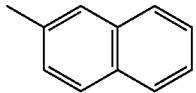 |
| 5 | 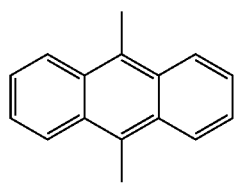 | 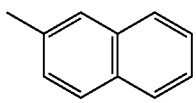 |
| 6 | 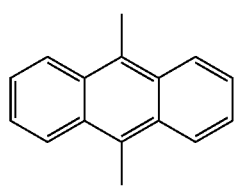 | 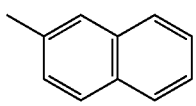 |
| 7 | 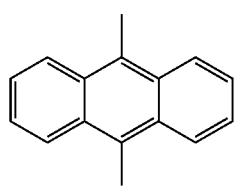 | 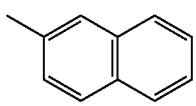 |
| 8 | 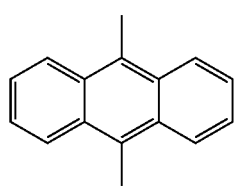 | 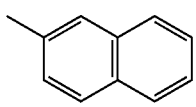 |

Among the above specific examples, Compounds (1-1), (1-5), (1-7), (2-1), (3-1), (4-2), (4-6), (7-2), (7-7), (7-8), (7-9) and (9-7) are particularly preferable.

The novel derivative of heterocyclic compound having nitrogen atom represented by general formulae (I), (II) or (III) of the present invention is preferably employed as a material for the organic EL devices.

Employing the compound of the present invention as at least one layer among the organic compound layers of the organic EL devices enables to achieve elevation of luminance and current efficiency.

It is preferable that the compound of the present invention is employed to a light emitting zone, a light emitting layer and/or an electron transporting layer of the organic EL device. In particular, it is preferable that the compound of the present invention is employed as an electron injecting material and/or an electron transporting material. Further, it is preferable that a layer containing the electron injecting material and/or the electron transporting material comprises reductive dopant.

The light emitting zone means the whole area containing a luminescent material which emits light when an electric field is applied to the organic EL device. Currently, the organic EL device has, in general, a laminated structure of each thin film comprising materials having different function and role, and in many cases, only an organic thin film layer named as a light emitting layer comprises the luminescent material. In this case, the light emitting layer corresponds to the light emitting zone. Further, explanations about the light emitting layer, the electron transporting layer and the electron injecting material will be described below.

Following is a description regarding a device structure about the organic EL device of the present invention.

The organic EL device of the present invention comprises at least one of organic compound layers containing a light emitting layer sandwiched between a pair of electrodes, wherein the organic compound layers comprises at least one layer containing a derivative of heterocyclic compound having nitrogen atom represented by any one of general formulae (I), (II) and (III) of the present invention.

Typical examples of the construction of the organic EL device of the present invention include:
anode/hole injecting layer/light emitting layer/electron injecting layer/cathode type;
anode/light emitting layer/electron injecting layer/cathode type;
anode/hole injecting layer/light emitting layer/cathode type; and
anode/light emitting layer/cathode type.
However, the construction of the organic EL device is not limited to those described above as the examples.

It is preferable for the organic EL device of the present invention to employ the compound of the present invention as a constituting material for the light emitting layer and/or the electron injecting layer. Although the hole injecting layer or the electron injecting layer is not always necessary for the device structure, an organic EL device having these layers has an advantage of improving light emitting property. Further, the hole injecting layer, the light emitting layer and the electron injecting layer may be mixedly sandwiched between a pair of electrodes. Furthermore, a mixed layer may be made with the use of a binder such as a high molecular compound in order that each constituting component exists stably.

An explanation about an organic EL device of anode/hole injecting layer/light emitting layer/electron injecting layer/cathode type example of the present invention will be described hereinunder. In general, the organic EL device is produced on a substrate which transmits light. The substrate which transmits light is the substrate which supports the organic EL device. As the substrate which transmits light, for example, glass sheet, synthetic resin sheet and quartzes are advantageously employed.

As the anode, an electrode made of a material such as a metal, an alloy, a conductive compound and a mixture of these materials which has a great work function (4 eV or more) is preferable. Specific examples of the material for the anode include metals such as Au and conductive materials such as CuI, ITO (indium tin oxide), $SnO_2$, ZnO and In—Zn—O. The anode can be prepared by forming a thin film of the electrode material described above in accordance with a process such as the vapor deposition process and the sputtering process. When the light emitted from the light emitting layer is obtained through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of from 10 nm to 1 m and preferably in the range of from 10 to 200 nm although the preferable range may be different depending on the adopted material.

As the cathode, an electrode made of a material such as a metal, an alloy, a conductive compound and a mixture of these materials which has a small work function (4 eV or smaller) is employed. Specific examples of the material for the cathode include sodium, sodium-potassium alloys, magnesium, magnesium-silver alloys, lithium, magnesium/copper mixture, magnesium-indium alloys, $Al/Al_2O_3$, indium, aluminum-lithium alloys, etc. The cathode can be prepared by forming a thin film of the electrode material described above in accordance with a process such as the vapor deposition process and the sputtering process. It is also preferable that the sheet resistivity of the cathode is several hundred $\Omega/\square$ or smaller. The thickness of the cathode is, in general, selected in the range of from 10 nm to 500 nm and preferably in the range of from 50 to 200 nm. Additionally, it is convenient that either the anode or the cathode of the organic EL device is transparent or translucent in order to transmit light because an efficiency of light emission improves.

It is preferable to employ the foregoing compound of the present invention as the light emitting material composing the light emitting layer in the organic EL device of the present invention. In the case where the compound of the present invention is employed as the light emitting material, the compound may be used alone or in combination with any of publicly known light emitting materials. In the case where the compound of the present invention is employed for other than the light emitting layer, the light emitting material in the light emitting layer is not particularly restricted but may be selectively employed in option from among the conventional well known light emitting materials. For example, polycyclic condensed aromatics, fluorescent whitening agents such as benzoxazole base, benzthiazole base, benzimidazole base or so, and compounds having favorable thin film formation property such as metal chelated oxanoid compound, distyrylbenzene-based compound and so on are employed as the light emitting material. Examples of the polycyclic condensed aromatics include condensed ring light emitting substances containing anthracene, naphthalene, phenanthrene, pyrene, chrysene and perylene backbone structure, other condensed ring light emitting substances containing about 8 condensed rings, etc. Specifically, 1,1,4,4-tetraphenyl-1,3-butadiene, 4,4'-(2,2-diphenyl vinyl) biphenyl and so on are employable as the light emitting material. The light emitting layer may be composed of single layer comprising one or more kind of these light emitting materials or may be laminated with a light emitting layer comprising another kind of compound.

A hole injecting layer in the organic EL device of the present invention consists of a hole transfer compound, and is capable of transferring hole which is injected from the anode to the light emitting layer. By intervening the hole injecting layer between the anode and the light emitting layer, large numbers of holes are injected into the light emitting layer even though a relatively lower electric field is applied. Moreover, because electrons injected into the light emitting layer from the cathode or the electron injecting layer are, with the influence of an electronic barrier existing on interfacial area between the light emitting layer and the hole injecting layer, a superior organic EL device with favorable light emitting property such as improving an efficiency of light emission can be obtained. The hole transfer compound used for such a hole injecting layer which is deployed between the two electrodes is capable of transferring holes adequately into the light emitting layer when the holes are injected from the anode. A compound which exhibits, for example, a mobility of holes of at least $10^{-6}$ cm$^2$/V·second under application of an electric field of from $10^4$ to $10^6$ V/cm is preferable as the hole transfer compound. With regard to the hole transfer compound, it is not particularly specified as long as it has the above favorable light emitting property. Namely, any compound may be selectively employed as the hole transfer compound from among compounds such as used in custom as charge injection and charge transport material of holes among a light conducting material or publicly known as the hole injecting layer of the organic EL device.

Examples of the above hole transfer compound include copper phthalocyanine, N,N,N',N'-tetraphenyl-4,4'-diaminophenyl, N,N'-diphenyl-N,N'-di(3-methylphenyl)-4,4'-diaminobiphenyl (TPDA), 2,2-bis(4-di-p-tolylaminophenyl) propane, 1,1-bis(4-di-p-tolylaminophenyl)cyclohexane, N,N,N',N'-tetra-p-tolyl-4,4'-diaminobiphenyl, etc. Further, crystals of inorganic semiconductor such as Si, SiC or CdS and amorphous material may be also employed as the hole transfer compound. The hole injecting layer may be composed of single layer comprising one or more kind of these hole injecting materials or may be laminated with a hole injecting layer comprising another kind of compound.

An electron injecting layer in the organic EL device of the present invention consists of an electron transfer material, and is capable of transferring electron which is injected from the cathode to the light emitting layer. In the organic EL device of the present invention, it is preferable to employ the foregoing compound of the present invention as the electron injecting material. In the case where the compound of the present invention is employed for other than the electron injecting layer, the electron injecting material is not particularly restricted but may be selectively employed in option from among the conventional well known electron injecting material compounds.

As a preferable embodiment of the organic EL device in the present invention, there is a device containing a reductive dopant in an electron transport zone or an interfacial zone between a cathode and an organic compound layer. In the organic EL device of the present invention, it is preferable to employ the foregoing compound of the present invention. The reductive dopant used in the present invention is defined as a compound which is added to the interfacial region between the electron injecting layer and the cathode and enhances the effect of electron injection. Examples of the reductive dopant include at least one compound selected from alkali metals, alkali metal complexes, alkali metal compounds, alkaline earth metals, alkaline earth metal complexes, alkaline earth metal compounds, rare earth metals, rare earth metal complexes and rare earth metal compounds.

Preferable reductive dopant has a work function of 2.9 eV or smaller. Specific examples of preferable reductive dopant include at least one kind or more of the alkaline metal selected from a group consisting of Na (the work function: 2.36 eV), K (the work function: 2.28 eV), Rb (the work function: 2.16 eV) and Cs (the work function: 1.95 eV). Further, the examples include at least one kind or more of the alkaline earth metal selected from a group consisting of Ca (the work function: 2.9 eV), Sr (the work function: 2.0-2.5 eV) and Ba (the work function: 2.52 eV). Among these, more preferable reductive dopants include at least one kind or more selected from the group consisting of K, Rb and Cs, the latter Rb or Cs being farther more preferable and the last Cs being the most preferable. These alkaline metals have particularly high reducing capability, and only an addition of relatively small amount of them into an electron injection zone enables to achieve both improvement of luminance and lifetime extension of the organic EL device. In particular, a combination including Cs, for example, combinations of Cs and Na, Cs and K, Cs and Rb or Cs, Na and K are preferable. Containing Cs in combination enables to reveal reducing capability effectively, and the addition into the electron injection zone achieves both improvement of luminance and lifetime extension of the organic EL device. Also, aside from the alkali metals, even an employment of at least one or more kinds of metal compound selected from the group consisting of alkali metal chalcogenide, alkaline earth metal chalcogenide, halide of alkali metal and halide of alkaline earth metal also achieves similar effects. Still further, an employment of alkali metal organic complexes or alkaline earth metal organic complexes also achieves similar effects.

In the organic EL device of the present invention, an electron injecting layer comprising electric insulating material, semiconductor and inorganic compound may be disposed between the cathode and the organic layer. The disposition of the electron injecting layer enables to effectively prevent a leak of electric current and to improve the electron injection property. It is preferable that at least one metal compound selected from the group consisting of alkali metal chalcogenides, alkaline earth metal chalcogenides, alkali metal halides and alkaline earth metal halides is used as the insulating material. It is preferable that the electron injecting layer is constituted with the above alkali metal chalcogenide since the electron injecting property can be improved. Preferable examples of the alkali metal chalcogenide include Li$_2$O, LiO, Na$_2$S, Na$_2$Se and NaO. Preferable examples of the alkaline earth metal chalcogenide include CaO, BaO, SrO, BeO, BaS and CaSe. Preferable examples of the alkali metal halide include LiF, NaF, KF, LiCl, KCl and NaCl. Preferable examples of the alkaline earth metal halide include fluorides such as CaF$_2$, BaF$_2$, SrF$_2$, MgF$_2$ and BeF$_2$ and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron injection layer is in the form of a fine crystalline or amorphous insulating thin film. When the electron injection layer is constituted with the above inorganic compound, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

The electron injecting layer in the organic EL device of the present invention can be formed in accordance with the publicly known thin-film formation method such as the vacuum vapor deposition process, the spin coating process, the casting process or the LB process employing the compound of the present invention or other electron injection material. Although the thickness of the electron injecting layer is not particularly limited, the thickness is usually from 5 nm to 5 µm. The electron injecting layer may be composed of single layer comprising one or more kind of these electron injecting materials or may be laminated with an electron injecting layer comprising another kind of compound. Furthermore, inorganic hole injection materials such as p type-Si and p type-SiC, inorganic electron injection materials such as n type α-Si and n type α-SiC are employed as the electron injection material for composing electron injecting layer. Specific examples of the above electron injection material correspond to inorganic semiconductors disclosed in International Patent Publication No. WO 90/05998, etc.

Following is a description regarding a preparing method about the organic EL device of the present invention. An explanation about an organic EL device of anode/hole injecting layer/light emitting layer/electron injecting layer/cathode type example of the present invention will be described as a preferred embodiment hereinunder. First, a thin film consisting of a desired electrode substance, for example, a substance for the anode is formed over a suitable substrate so as to finally achieve a film thickness of 1 µm or thinner, preferably within a range from 10 nm to 200 nm in accordance with a vapor deposition method, a sputtering method, etc. Then, the hole injecting layer, the light emitting layer and the electron injecting layer which are all EL device composing elements are made by successively forming thin films consisting of each composing material into multi layers. With regard to a thin film formation process to be used, there are the spin coating process, the casting process or the vapor deposition process as the foregoing description. A vacuum vapor deposition process is preferable because a uniform film can be easily obtained and the possibility of formation of pin holes is small. In the case where the vacuum vapor deposition process is adopted as the thin film formation process, the vapor deposition condition is different according to the kind of the compound employed, a crystal structure or an association structure each as an object of molecular pile membrane. However, it is generally preferable to appropriately select among port heat temperature of 50 to 400° C., vacuum of $10^{-6}$ to $10^{-3}$ Pa, vapor deposition rate of 0.01 to 50 nm/second, substrate temperature of −50 to 300° C., and film thickness of 5 nm to 5 µm respectively. After forming the above layers, a thin film consisting of a cathode substance is formed thereupon into a film thickness of 1 µm or thinner, preferably within a range from 50 to 200 nm, in accordance with, for example, the vapor deposition process or the sputtering process, thereby making cathode and resultantly obtaining a desired organic EL device. Additionally, in preparation of the organic EL device, reversing the formation order, a formation in order of the cathode, the electron injecting layer, the light emitting layer, the hole injecting (transporting) layer and the anode may be applicable.

Further, a preparation of an organic EL device of the anode/the light emitting layer/the cathode type wherein a hole injecting layer, a light emitting layer and an electron injecting layer as coexisting sandwiched between a pair of electrode is as the following: For example, forming a thin film consisting of anode substance over a suitable substrate, making a light emitting layer (or, a light emission area) by applying or dip coating a solution comprising a hole injection material, a light emitting material, electron injection material and a binder such as polyvinylcarbazole, polycarbonate, polyacrylate, polyester and polyether or so and, thereupon, forming a film consisting of cathode substance. After further vacuum vapor deposition of device materials which correspond to the light emitting layer or the electron injecting layer over the formed light emitting layer, the film consisting of cathode substance may be formed thereupon.

The organic EL device which can be produced as described above emits light when a direct voltage of 3 to 50 V is applied in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be employed.

Employing the derivative of heterocyclic compound having nitrogen atom of the present invention for the organic compound layer, particularly for the electron injecting layer, adhesion between the organic compound layer containing the compound of the present invention and the electrode (particularly, cathode) in the organic EL device of a the present invention is improved.

The organic EL device of the present invention prepared as the foregoing description achieves elevated luminance and excellent efficiency of light emission.

The present invention will be described more specifically with reference to examples and synthesis examples in the following. However, the present invention is not limited to the examples.

Synthesis Example 1

Synthesis of Compound (1-7)

(1) Synthesis of 2-(4-bromophenyl)-1-phenyl-1H-benzimidazole

Suspending 3.0 g (15 mmol) of 4-bromobenzoic acid into 30 milliliter of 1,2-dichloroethane, adding 2.7 g (23 mmol) of thionyl chloride and 3 drops of N,N-dimethylformamide, the resultant solution was stirred with heating at the temperature of about 50° C. for 1 hour and 30 minutes until benzoic acid as the material disappeared. After completion of the reaction, removing the solvent and excess thionyl chloride by distillation, dissolving the resultant acid chloride into 30 milliliter of N-methylpyrrolidone, adding 2.8 g (15 mmol) of N-phenyl-1,2-phenylenediamine, the resultant solution was stirred at room temperature for a night. After completion of the reaction, adding water and filtering the precipitated solid, further washing with water and by drying under reduced pressure, 5.2 g of 4-bromo-N-(2-phenylamino-phenyl)-benzamide was obtained.

The benzamide was stirred with heating under reduced pressure (about 20 mmHg) and at the temperature of about 300° C. for 30 minutes. After completion of the reaction, the resultant solution was further dissolved in dichloro-methane, and by refining with the use of silicagel column chromatography, 3.5 g of 2-(4-bromophenyl-1-phenyl-1H)-benzimidazole was obtained (yield: 80%).

(2) Synthesis of 2-[4-(10-naphthalene-2-yl-anthracene-9-yl)-phenyl]-1-phenyl-1H-benzimidazole (Compound (1-7))

Dissolving 4.0 g (11 mmol) of 2-(4-bromophenyl)-1-phenyl-1H-benzimidazole, 4.0 g (11 mmol) of 10-naphthalene-2-yl-anthracene-9-boronic acid and 0.27 g of tetrakis (triphenylphosphine) palladium into 40 milliliter of 1,2-dimethoxyethane, adding 18 milliliter of 2.0M sodium carbonate aqueous solution, the resultant suspension was refluxed with heating for 7 hours. After completion of the reaction, separation with filtration was carried out and resultant crystals were washed with water and methanol, thereby obtaining 5.1 g of yellowish white solids (yield: 78%). As a result of mass spectrum (MS) analysis, it was recognized that the yellowish white solids were identified as the aimed substance and that m/e=572 for molecular weight of 572.23.

Synthesis Example 2

Synthesis of Compound (4-2)

(1) Synthesis of 2-(3-bromophenyl)-1-phenyl-1H-benzimidazole

Almost the same procedure as step (1) in Synthesis Example 1 was carried out except that 3-bromobenzoic acid was employed instead of 4-bromobenzoic acid, 3.8 g of 2-(3-bromophenyl)-1-phenyl-1H-benzimidazole was obtained (yield: 81%).

(2) Synthesis of 2-[3-(10-naphthalene-2-yl-anthracene-9-yl)-phenyl]-1-phenyl-1H-benzimidazole (Compound (4-2))

Almost the same procedure as step (2) in Synthesis Example 1 was carried out except that 2-(3-bromophenyl)-1-phenyl-1H-benzimidazole obtained in the above step (1) was used instead of -(4-bromo-phenyl)-1-phenyl-1H-benzimidazole, resultantly obtaining 3.7 g of yellowish white solids (yield: 74%). As a result of MS analysis, it was recognized that the yellowish white solids were identified as the aimed substance and that m/e=572 for molecular weight of 572.23.

Synthesis Example 3

Synthesis of Compound (1-1)

(1) Synthesis of 2-(4-iodophenyl-1-phenyl-1H-benzimidazole

Suspending 5.0 g (20 mmol) of 4-iodobenzoic acid into 50 milliliter of 1,2-dichloroethane, added 3 drops of N,N-dimethylformamide. Further adding 3.6 g (30 mmol) of thionyl chloride, the resultant suspension was refluxed with heating for 2 hours. Subsequently, removing the solvent by distillation, the residue was dissolved into 50 milliliter of N-methylpyrrolidone and then, further adding 3.7 g (20 mmol) of N-phenyl-1,2-phenylenediamine, the resultant solution was stirred at room temperature for 5 hours. After completion of the reaction, adding water and filtering the precipitated solid, washing with water and further with methanole, 8.0 g of crude 4-iodo-N-(2-phenylamino-phenyl)-benzamide was obtained.

Dispersing 4.5 g (11 mmol) of the obtained crude 4-iodo-N-(2-phenylamino-phenyl) benzamide and 0.57 g (3 mmol) of p-toluenesulfonic acid 1 hydrate into 45 milliliter of xylene, the resultant solution was refluxed with heating for 3 hours. After completing the reaction, adding water and then, after filtering the precipitated solid, further adding ethyl acetate and water to the resultant solid, an organic layer was extracted. The organic layer was washed with 5% potassium carbonate aqueous solution, water and a solution of sodium chloride, followed by drying with sodium sulfate. Removing the solvent by distillation and by washing the resultant solid with hexane, 3.9 g of 2-(4-iodophenyl)-1-phenyl-1H-benzimidazole was obtained (yield: 91%).

(2) Synthesis of 1-phenyl-2-[4-(10-phenyl-anthracene-9-yl)-phenyl]-1H-benzimidazole (Compound (1-1))

Almost the same procedure as step (2) in Synthesis Example 1 was carried out except that corresponding 10-phenyl anthracene-9-boronic acid was used instead of 10-naphthalene-2-yl-anthracene-9-boronic acid, and that corresponding 2-(4-iodophenyl)-1-phenyl-1H-benzimidazole was used instead of 2-(4-bromophenyl)-1-phenyl-1H-benzimidazolein, resultantly obtaining an aimed Compound (1-1) (yield: 59%). As a result of MS analysis, it was recognized that m/e=522 for aimed substance's molecular weight of 522.21.

Synthesis Example 4

Synthesis of Compound (2-1)

(1) Synthesis of 2-(4-iodophenyl)-1-methyl-1H-benzimidazole

Suspending 10.0 g (41 mmol) of 4-iodobenzoic acid into 100 milliliter of 1,2-dichloroethane, added 3 drops of N,N-dimethylformamide. Further adding 7.3 g (61 mmol) of thionyl chloride, the resultant suspension was refluxed with heating for 2 hours. Subsequently, removing the solvent by distillation, the residue was dissolved into 100 milliliter of N-methylpyrrolidone and then, further adding 5.0 g (41 mmol) of N-phenyl-1,2-phenylenediamine, the resultant solution was stirred at room temperature for 5 hours. After completing the reaction, adding water and then, after filtering the precipitated solid, further adding ethyl acetate and water to the resultant solid, an organic layer was extracted (Insoluble substances were separated by filtration.). The organic layer was washed with 5% potassium carbonate aqueous solution, water and a solution of sodium chloride, followed by drying with sodium sulfate. Removing the solvent by distillation, a mixture of crude 4-iodo N-(2-methylamino-phenyl) benzamide and crude N-(2-aminophenyl)-4-iodo-N-methyl-benzamide in an amount of 11 g was obtained.

Dispersing 11 g (31 mmol) of the resultant mixture and 1.75 g (9 mmol) of p-toluenesulfonic acid 1 hydrate into 100 milliliter of xylene, the resultant solution was refluxed with heating for 7 hours. After completion of the reaction, the resultant solution was naturally cooled and adding 5% potassium carbonate aqueous solution and toluene, an organic layer was extracted. The organic layer was washed with 5% potassium carbonate aqueous solution, water and a solution of sodium chloride, followed by drying with sodium sulfate. Removing the solvent by distillation and refining the resultant brown oil with the use of a silicagel column chromatography (eluent hexane/ethyl acetate=3/1) 2.7 g of an aimed 2-(4-iodophenyl-1-methyl-1H-benzimidazole (yield: 20%).

(2) Synthesis of 1-methyl-2-[4-(10-naphthalene-2-yl-anthracene phenyl]-1H-benzimidazole (Compound (2-1))

Almost the same procedure as step (2) in Synthesis Example 1 was carried out except that corresponding 2-(4-iodephenyl)-1-methyl-1H-benzimidazole was used instead of 2-(4-bromophenyl)-1-phenyl-1H-benzimidazole, resultantly obtaining an aimed compound (Compound (2-1) (yield: 33%). As a result of MS analysis, it was recognized that m/e=m/e=510 for aimed substance's molecular weight of 510.21.

Synthesis Example 5

Synthesis of Compound (3-1)

(1) Synthesis of 2-nitro-N-pyridyl aniline

Under the atmosphere of nitrogen gas, 15.0 g (109 mmol) of 2-nitroaniline, 17.2 g (109 mmol) of 2-bromopyridine, 2.06 g (10.9 mmol) of copper iodide and 30 g (218 mmol) of potassium carbonate were stirred with heating at the temperature of 160° C. for 9 hours. The reacted solution was cooled down to room temperature, diluted with ethyl acetate and filtered. After concentrating the filtrate, it was refined with silicagel column chromatography, and 6.30 g of 2-nitro-N-pyridyl aniline was obtained (yield: 27%).

(2) Synthesis of 2-(2-pyridylamino)-4'-bromobenzanilide

Dissolving 6.3 g (29.2 mmol) of 2-nitro-N-pyridyl aniline obtained in the above step (1) into 50 milliliter of tetrahydrofuran, and during agitation under the atmosphere of nitrogen gas and at room temperature, a solution provided by mixing 26 g (146 mmol) of sodium hydrosulfite into 90 milliliter of water was dropped. Further, adding 5 milliliter of methanol, the resultant solution was stirred for 3 hours. Subsequently, adding 50 milliliter of ethyl acetate and then, a solution provided by mixing 5.0 g (59.5 mmol) of sodium hydrogen carbonate and 50 milliliter of water was further added. Furthermore, a solution provided by mixing 6.6 g (30.0 mmol) of 4-bromobenzoyl chloride/20 milliliter of ethyl acetate was dropped and the resultant solution was stirred at room temperature for 5 hours. After separating the precipitated solid by filtration, the solid was washed with water and methanol, then, 5.5 g of 2-(2-pyridylamino)-4'-bromobenzanilide was obtained (yield: 51%).

(3) Synthesis of 1-(2-pyridyl)-2-(4-bromophenyl)-1H-benzimidazole

Suspending 5.5 g (15.0 mmol) of 2-(2-pyridylamino)-4'-bromobenzanilide obtained in the above step (2) into 60 milliliter of xylene, and adding 0.86 g (4.5 mmol) of p-toluenesulfonic acid 1 hydrate, the resultant solution was azeotropically dehydrated while refluxing with heating for 8 hours. The reacted solution was cooled down to room temperature, and the solvent was removed by distillation. Dissolving the resultant solid into ethyl acetate, and after sequentially washing with water, with 10% potassium carbonate aqueous solution and with saturated solution of sodium chloride, it was dried with sulfuric anhydride magnesium, followed by removing the solvent by distillation under reduced pressure, 3.5 g of 1-(2-pyridyl)-2-(4-bromophenyl)-1H-benzimidazole was obtained (yield: 67%).

(4) Synthesis of 2-[4-(10-naphthalene-2-yl-anthracene-9-yl)-phenyl]-1-(2-pyridyl)-1H-benzimidazole (Compound (3-1))

Dissolving 3.5 g (10 mmol) of 1-(2-pyrizyl)-2-(4-bromophenyl)-1H-benzimidazole obtained in the above step (3), 4.2 g (12.1 mmol) of 10-naphthalene-2-yl-anthracene-9-boronic acid and 0.23 g (0.20 mmol) of tetrakis (triphenylphosphine) palladium into 60 milliliter of 1,2-dimethoxyethane, adding 30 milliliter of 2.0M sodium carbonate aqueous solution, the resultant suspension was refluxed with heating for 8 hours. After completion of the reaction, separation with filtration was carried out and resultant crystals were washed with water, methanol and toluene, thereby obtaining 5.0 g of greenish white solids (yield: 86%). As a result of MS analysis, it was recognized that the greenish white solids were identified as the aimed substance and that m/e=573 for molecular weight of 573.22.

Synthesis Example 6

Synthesis of Compound (4-6)

(1) Synthesis of 2-(5-bromopyridine-3-yl)-1-phenyl-1H-benzimidazole

Almost the same procedure as the above step (1) of Synthesis Example 1 was carried out except that 5-bromonicotinic acid was employed instead of 4-bromobenzoic acid, 5.93 g of 2-(5-bromopyridine)-1-phenyl-1H-benzimidazole was obtained (yield: 49%).

(2) Synthesis of 2-[5-(10-naphthalene-2-yl-anthracene-9-yl)-pyridine-3-yl]-1-phenyl-1H-benzimidazole (Compound (4-6))

Almost the same procedure as step (2) in Synthesis Example 1 was carried out except that corresponding 2-(5-bromopyridine-3-yl)-1-phenyl-1H-benzimidazole was used instead of 2-(4-bromophenyl-phenyl-1H-benzimidazole, resultantly obtaining an aimed compound (Compound (4-6) (yield: 36%). As a result of MS analysis, it was recognized that m/e=573 for aimed substance's molecular weight of 573.22.

Synthesis Example 7

Synthesis of Compound (7-2)

(1) Synthesis of 4-bromo-2-nitrodiphenylamine

A mixture made from 10 g (35.6 mmol) of 2,5-dibromo nitrobenzene, 8.8 g (107 mmol) of sodium acetate and 6.6 g (71 mmol) of aniline was stirred with heating at the temperature of 160° C. under the atmosphere of nitrogen gas for 9 hours. The reacted solution was cooled down to room temperature, diluted with ethyl acetate and filtered. After concentrating the filtrate, it was refined with silicagel column chromatography, and 9.9 g of 4-bromo-2-nitrodiphenylamine was obtained (yield: 63%).

(2) Synthesis of 5-bromo-2-phenylamino benzanilide

Dissolving 9.9 g (38.8 mmol) of 4-bromo-2-nitrodiphenyl amine obtained in the above step (1) into 75 milliliter of tetrahydrofuran, and during agitation under the atmosphere of nitrogen gas and at room temperature, a solution provided by mixing 30 g (170 mmol) of sodium hydrosulfite into 100 milliliter of water was dropped. Further, adding 10 milliliter of methanol, the resultant solution was stirred for 3 hours. Subsequently, adding 75 milliliter of ethyl acetate and then, a solution provided by mixing 5.7 g (67.8 mmol) of sodium hydrogen carbonate and 60 milliliter of water was further added. Furthermore, a solution provided by mixing 4.8 g (34 mmol) of benzoyl chloride/25 milliliter of ethyl acetate was dropped and the resultant solution was stirred at room temperature for 5 hours. Extracting the resultant mixture with ethyl acetate, and after sequentially washing with water, with 10% potassium carbonate aqueous solution and with saturated solution of sodium chloride, it was dried with sulfuric anhydride magnesium, followed by removing the solvent by distillation under reduced pressure, 5.6 g of 5-bromo-2-phenylamino benzanilide was obtained (yield: 45%).

(3) Synthesis of
5-bromo-1,2-diphenyl-1H-benzimidazole

Suspending 5.6 g (15 mmol) of 5-bromo-2-phenylamino benzanilide obtained in the above step (2) into 60 milliliter of xylene, and adding 0.88 g (4.6 mmol) of p-toluenesulfonic acid 1 hydrate, the resultant solution was azeotropically dehydrated while refluxing with heating for 5 hours. The reacted solution was cooled down to room temperature, and the solvent was removed by distillation under reduced pressure. The resultant solid was washed with ethanol and 2.5 g of 5-bromo-1,2-diphenyl-1H-benzimidazole was obtained (yield: 46%).

(4) Synthesis of 1,2-diphenyl-5-(10-naphthalene-2-yl-anthracene-9-yl)-1H-benzimidazole (Compound (7-2))

Dissolving 2.5 g (7.1 mmol) of 5-bromo-1,2-diphenyl-1H-benzimidazole obtained in the above step (3), 3.0 g (8.5 mmol) of 10-naphthalene-2-yl-anthracene-9-boronic acid and 0.16 g (0.14 mmol) of tetrakis (triphenylphosphine) palladium into 60 milliliter of 1,2-dimethoxyethane, adding 30 milliliter of 2.0M sodium carbonate aqueous solution, the resultant suspension was refluxed with heating for 8 hours. After completion of the reaction, separation with filtration was carried out and resultant crystals were washed with water, methanol and toluene, thereby obtaining 2.0 g of greenish white solids (yield: 49%). As a result of MS analysis, it was recognized that the yellowish white solids were identified as the aimed substance and that m/e=572 for molecular weight of 572.23.

Synthesis Example 8

Synthesis of Compound (9-7)

(1) Synthesis of
(4-bromophenyl)-(2-nitrophenyl)amine

A mixture made from 10 g (49.5 mmol) of 2-bromo nitrobenzene, 13 g (163 mmol) of sodium acetate and 10 g (59 mmol) of 4-bromo aniline was stirred with heating at the temperature of 180° C. under the atmosphere of nitrogen gas for 8 hours. The reacted solution was cooled down to room temperature, diluted with ethyl acetate and filtered. After concentrating the filtrate, and by washing the residue with methanol 3.8 g of (4-bromophenyl)-(2-nitrophenyl) amine was obtained as orange crystals (yield: 22%).

(2) Synthesis of
N-[2-(4-bromophenylamino)phenyl]benzamide

Dissolving 3.8 g (13 mmol) of (4-bromophenyl)-(2-nitrophenyl) amine obtained in the above step (1) into 30 milliliter of tetrahydrofuran, and during agitation under the atmosphere of nitrogen gas and at room temperature, a solution provided by mixing 11 g (64 mmol) of sodium hydrosulfite into 30 milliliter of water was dropped. Subsequently, after stirring for 5 hours, adding 20 milliliter of ethyl acetate and then, a solution provided by mixing 2.2 g (26 mmol) of sodium hydrogen carbonate and 20 milliliter of water was further added. Furthermore, a solution provided by mixing 2.5 g (18 mmol) of benzoyl chloride/10 milliliter of ethyl acetate was dropped and the resultant solution was stirred at room temperature for 1 hour. Extracting the resultant mixture with ethyl acetate, and after sequentially washing with 10% potassium carbonate aqueous solution, with water and with a saturated solution of sodium chloride, it was dried with sulfuric anhydride magnesium, followed by removing the solvent by distillation under reduced pressure, 2.1 g of N-[2-(4-bromophenyl amino)phenyl]benzamide was obtained (yield: 45%).

(3) Synthesis of
1-(4-bromophenyl)-2-phenyl-1H-benzimidazole

Suspending 2.1 g (5.7 mmol) of N-[2-(4-bromophenylamino)phenyl]benzamide obtained in the above step (2) into 30 milliliter of xylene, and adding 0.6 g (2.9 mmol) of p-toluenesulfonic acid 1 hydrate, the resultant solution was azeotropically dehydrated while refluxing with heating for 3 hours. After naturally cooling the reacted solution, ethyl acetate, dichloromethane and water were added to the reacted solution, followed by separating an insoluble substance by filtration. Extracting an organic layer from mother liquor, the organic layer was washed with water and a saturated solution of sodium chloride and then, dried with anhydrous sodium sulfate, followed by removing the solvent by distillation under reduced pressure. Refining the residue with silicagel column chromatography, 1.0 g of 1-(4-bromophenyl)-2-phenyl-1H-benzimidazole was obtained as white crystals with a slight pink color (yield: 52%).

(4) Synthesis of 1-[4-(10-naphthalene-2-yl-anthracene-9-yl) phenyl]-2-phenyl-1H-benzimidazole (Compound (9-7))

Dissolving 1.0 g (2.9 mmol) of 1-(4-bromophenyl)-2-phenyl-1H-benzimidazole obtained in the above step (3), 1.1 g (3.1 mmol) of 10-naphthalene-2-yl-anthracene-9-boronic acid and 0.1 g (0.09 mmol) of tetrakis (triphenylphosphine) palladium into 15 milliliter of 1,2-dimethoxyethane and 2 milliliter of toluene, adding 5 milliliter of 2.0M sodium carbonate aqueous solution, the resultant suspension was refluxed with heating for 7 hours. After completion of the reaction, separation with filtration was carried out and resultant crystals were washed with water and methanol, thereby obtaining 1.45 g of cream color solids (yield: 89%). As a result of MS analysis, it was recognized that the cream color solids were identified as the aimed substance and that m/e=572 for molecular weight of 572.23.

Synthesis Example 9

Synthesis of a Compound (4-5)

(1) Synthesis of 6-bromo-2'-(N-phenylamino)-picoline anilide

Suspending 5.1 g (25 mmol) of 6-bromo picolinic acid into 70 milliliter of 1,2-dichloroethane, adding 4.2 g (35 mmol) of thionyl chloride and 3 drops of N,N-dimethylformamide, the resultant solution was cycled with heating for 4 hours. After completion of the reaction, the solvent was removed under reduced pressure, thereby obtaining 6-bromo picolinoyl chloride.

Dissolving 4.4 g (24 mmol) of N-phenyl-1,2-phenylenediamine into 30 milliliter of N-methylpyrrolidone, 10 milliliter of 6-bromo picolinoyl chloride/N-methylpyrrolidone was dropped under cooling with ice. The resultant solution was further stirred at room temperature for 4 hours. After completion of the reaction, the reacted solution was poured into 400 milliliter of water and the resultant solution was further stirred. The resultant solids were separated by filtration, washed with water and methanol, dried under reduced pressure, thereby obtaining 4.5 g of 6-bromo-2'-(N-phenylamino)-picoline anilide (yield: 49%).

(2) Synthesis of 2-(6-bromopyridyl-2-yl)-1-phenyl-1H-benzimidazole

Suspending 4.5 g (12 mmol) of 6-bromo-2'-(N-phenylamino)-picoline anilide obtained in the above step (1) into 50 milliliter of xylene, and adding 0.70 g (3.7 mmol) of p-toluenesulfonic acid 1 hydrate, the resultant solution was azeotropically dehydrated while refluxing with heating for 6 hours. The reacted solution was cooled down to room temperature, and the solvent was removed by distillation. Dissolving the resultant solid into ethyl acetate, and after sequentially washing with water, with 10% potassium carbonate aqueous solution and with a saturated solution of sodium chloride, it was dried with sulfuric anhydride magnesium, followed by removing the solvent by distillation under reduced pressure, 3.0 g of 2-(6-bromopyridyl-2-yl)-1-phenyl-1H-benzimidazole was obtained (yield: 70%).

(3) Synthesis of 2-[6-(10-naphthalene-2-yl-anthracene-9-yl)-pyridyl-2-yl]-1-phenyl-1H-benzimidazole (Compound (4-5))

Dissolving 3.0 g (8.6 mmol) of 2-(6-bromopyridyl-2-yl)-1-phenyl-1H-benzimidazole obtained in the above step (2), 3.6 g (10 mmol) of 10-naphthalene-2-yl-anthracene-9-boronic acid and 0.20 g (0.17 mmol) of tetrakis (triphenylphosphine) palladium into 60 milliliter of 1,2-dimethoxyethane, adding 30 milliliter of 2.0M sodium carbonate aqueous solution, the resultant suspension was refluxed with heating for 8 hours. After completion of the reaction, separation with filtration was carried out and resultant solids were washed with water, methanol and toluene, thereby obtaining 2.0 g of greenish white solids (yield: 41%). As a result of MS analysis, it was recognized that the greenish white solids were identified as the aimed substance and that m/e=573 for molecular weight of 573.22.

Synthesis Example 10

Synthesis of a Compound (11-1)

(1) Synthesis of 2-picolinic acid [2-(4-bromophenylamino)-phenyl]-amide

Dissolving 5.0 g (17 mmol) of (4-bromo-phenyl)-(2-nitrophenyl)-amine into 50 milliliter of tetrahydrofuran, an aqueous solution prepared by dissolving 15 g (86 mmol) of sodium dithionite into 60 milliliter of water was added. Subsequently, adding 10 milliliter of methanol, the resultant solution was stirred at room temperature for 3 hours. After recognizing that the color (orange) of the resultant solution almost disappeared, water was added, followed by extracting with ethyl acetate. After sufficiently drying an organic layer with sodium sulfate, the solvent was removed by distillation, and as a result, phenylenediamine was obtained. Dissolving the resultant phenylenediamine into 150 milliliter of ethyl acetate, an organic layer was extracted. Further, 5.4 g (68 mmol) of pyridine, 3.6 g (23 mmol) of 2-picolinic acid chloride hydrochloride and catalyst amount of 4-dimethylaminopyridine (DMAP) were added to the organic layer, and the resultant solution was stirred at room temperature for 3 hours, followed by left standing for a night. After completion of the reaction, adding water, separation with filtration was carried out for precipitated solids and then, they were sufficiently washed with water and methanol, thereby obtaining 3.8 g of 2-picolinic acid amide as white solid (yield: 60%).

(2) Synthesis of 1-(4-bromophenyl-2-pyridine-2-yl-1H-benzimidazole

The above 2-picolinic acid amide in an amount of 3.8 g (10 mmol) was stirred with heating under reduced pressure (about 20 mmHg) and at the temperature of about 300° C. for 30 minutes. After completion of the reaction, the resultant solution was further dissolved in dichloro-methane, and by refining with the use of silicagel column chromatography, 2.5 g of 1-(4-bromophenyl)-2-pyridine-2-yl-1H-benzimidazole (yield: 69%).

(3) Synthesis of 1-[4-(10-naphthalene-2-yl-anthracene-9-yl)-phenyl]-2-methyl-1H-benzimidazole (Compound (11-1))

Dissolving 1.2 g (3.4 mmol) of 1-(4-bromophenyl)-2-pyridine-2-yl-1H-benzimidazole, 1.2 g (3.4 mmol) of 10-naphthalene-2-yl-anthracene-9-boronic acid and 0.10 g of tetrakis (triphenylphosphine) palladium into 15 milliliter of 1,2-dimethoxyethane, adding 6 milliliter of 2.0M sodium carbonate aqueous solution, the resultant suspension was refluxed with heating for 7 hours. After completion of the reaction, the precipitated solids were dissolved into the dichloro-methane, washed with water and dried with sodium sulfate. Removing the solvent by distillation and by refining the resultant product with the use of a silicagel column chromatography (dichloro methane-ethyl acetate), 1.2 g of an yellowish white solids were obtained (yield: 61%). As a result of MS analysis, it was recognized that the yellowish white solids were identified as the aimed substance and that m/e=573 for molecular weight of 573.22.

Synthesis Example 11

Synthesis of Compound (12-2)

(1) Synthesis of N-[2-(4-bromophenyl amino)-phenyl]-acetamide

Dissolving 8.0 g (30 mmol) of (4-bromo-phenyl)-(2-nitrophenyl)-amine into 80 milliliter of tetrahydrofuran, an aqueous solution prepared by dissolving 24 g (0.14 mmol) of sodium dithionite into 100 milliliter of water was added. Subsequently, adding 10 milliliter of methanol, the resultant solution was stirred at room temperature for 3 hours. After recognizing that the color (orange) of the resultant solution almost disappeared, water was added, followed by extracting with ethyl acetate. After sufficiently drying an organic layer with sodium sulfate, the solvent was removed by distillation, and as a result, phenylenediamine was obtained. Dissolving the resultant phenylenediamine into 150 milliliter of ethyl acetate, an organic layer was extracted. Further, 3.0 g (38 mmol) of pyridine, 1.8 g (18 mmol) of acetic anhydride and catalyst amount of 4-dimethylaminopyridine (DMAP) were added to the organic layer, and the resultant solution was stirred at room temperature for 3 hours, followed by left standing for a night. After completion of the reaction, adding water, separation with filtration was carried out for precipitated solids and then, they were sufficiently washed with water and methanol, thereby obtaining 4.1 g of benzamide as white solid (yield: 49%).

(2) Synthesis of 1-(4-bromophenyl)-2-methyl-1H-benzimidazole

The above benzamide in an amount of 4.1 g (13 mmol) was stirred with heating under reduced pressure (about 20 mmHg) and at the temperature of about 300° C. for 30 minutes. After completion of the reaction, the resultant solution was further dissolved into dichloromethane, and by refining with the use of silicagel column chromatography, 3.8 g of 1-(4-bromophenyl)-2-methyl-1H-benzimidazole was obtained (yield: 97%).

(3) Synthesis of 1-[4-(10-naphthalene-2-yl-anthracene-9-yl)-phenyl]-2-methyl-1H-benzimidazole (Compound (12-2))

Dissolving 3.3 g (11 mmol) of 1-(4-bromophenyl)-2-methyl-1H-benzimidazole, 4.0 g (11 mmol) of 10-naphthalene-2-yl-anthracene-9-boronic acid and 0.27 g of tetrakis (triphenylphosphine) palladium into 40 milliliter of 1,2-dimethoxyethane, adding 20 milliliter of 2.0M sodium carbonate aqueous solution, the resultant suspension was refluxed with heating for 7 hours. After completion of the reaction, the precipitated solids were dissolved into the dichloromethane, washed with water and dried with sodium sulfate. Removing the solvent by distillation and by refining the resultant product with the use of a silicagel column chromatography (dichloro methane-ethyl acetate), 2.9 g of yellowish white solids were obtained (yield: 49%). As a result of MS analysis, it was recognized that the yellowish white solids were identified as the aimed substance and that m/e=510 for molecular weight of 510.21.

Synthesis Example 12

Synthesis of Compound (14-7)

(1) Synthesis of 5'-bromo-2'-(N-phenylamino)-acetanilide

Dissolving 4.5 g (15 mmol) of 4-bromo-2-nitrodiphenyl amine into 40 milliliter of tetrahydrofuran, and during agitation under the atmosphere of nitrogen gas and at room temperature, a solution provided by mixing 13.4 g (77 mmol) of sodium hydrosulfite into 45 milliliter of water was added. Further, adding 4 milliliter of methanol, the resultant solution was stirred for 3 hours. Subsequently, adding 40 milliliter of ethyl acetate and then, a solution provided by mixing 2.6 g (31 mmol) of sodium hydrogen carbonate and 30 milliliter of water was further added. The resultant solution was stirred for 30 minutes, followed by extracting with ethyl acetate. After removing a water layer, an organic layer was washed with water and with a saturated solution of sodium chloride and dried with magnesium sulfate. The solution was filtered and adding 2.4 g (31 mmol) of pyridine and further adding 2.0 g (19 mmol) of acetic anhydride, the resultant solution was stirred at room temperature for 5 hours. The solution was extracted with ethyl acetate, washed with 10% potassium carbonate aqueous solution and with saturated solution of sodium chloride successively, followed by drying with magnesium sulfuric anhydride. Removing the solvent by distillation under reduced pressure, 3.6 g of 5'-bromo-2'-(N-phenylamino)-acetanilide was obtained (yield: 77%).

(2) Synthesis of 5-bromo-2-methyl-1-phenyl-1H-benzimidazole

Suspending 3.6 g (12 mmol) of 5'-bromo-2'-(N-phenylamino)-acetanilide obtained in the above step (1) into 30 milliliter of xylene, and adding 0.68 g (3.6 mmol) of p-toluenesulfonic acid 1 hydrate, the resultant solution was azeotropically dehydrated while refluxing with heating for 5 hours. The reacted solution was cooled down to room temperature, and the solvent was removed by distillation. Dissolving the resultant solid into ethyl acetate, and after sequentially washing with water, with 10% potassium carbonate aqueous solution and with saturated solution of sodium chloride, it was dried with sulfuric anhydride magnesium, followed by removing the solvent by distillation under reduced pressure, 3.0 g of 5-bromo-2-methyl-1-phenyl-1H-benzimidazole was obtained (yield: 90%).

(3) Synthesis of 2-methyl-5-(10-naphthalene-2-yl-anthracene-9-yl)-1-phenyl-1H-benzimidazole (Compound (14-7))

Dissolving 3.0 g (11 mmol) of 5-bromo-2-methyl-1-phenyl-1H-benzimidazole obtained in the above step (2), 4.5 g (13 mmol) of 10-naphthalene-2-yl-anthracene-9-boronic acid and 0.25 g (0.22 mmol) of tetrakis (triphenylphosphine) palladium into 60 milliliter of 1,2-dimethoxyethane, adding 30 milliliter of 2.0M sodium carbonate aqueous solution, the resultant suspension was refluxed with heating under an atmosphere of argon gas for 8 hours. After completion of the reaction, separation with filtration was carried out and resultant solids were washed with water, methanol and toluene, thereby obtaining greenish white solids. Re-crystallizing the greenish white solids with the use of toluene, 2.0 g of yellowish green solids were obtained (yield: 37%). As a result of MS analysis, it was recognized that the yellowish green solids were identified as the aimed substance and that m/e=510 for molecular weight of 510.21.

Synthesis Example 13

Synthesis of Compound (15-8)

(1) Synthesis of 4-bromo-N-methyl-2-nitroaniline

Pouring 60 milliliter of acetic acid over 5.0 g (33 mmol) of N-methyl-2-nitroaniline and 5.9 g (33 mmol) of N-bromosuccinimide, the resultant solution was refluxed with heating for 7 hours. After completion of the reaction, the reacted solution was poured into 500 milliliter of water, and precipitated solids were separated with filtration. Dissolving the resultant solids into ethyl acetate, the resultant solution was dried with the use of magnesium sulfate. After filtration, the solvent was removed by distillation under reduced pressure, and after drying the solids under reduced pressure at room temperature, 7.1 g of 4-bromo-N-methyl-2-nitroaniline as orange solids were obtained (yield: 93%).

(2) Synthesis of 4'-bromo-N-methyl-2'-nitro-benzanilide

Dissolving 6.8 g (29 mmol) 4-bromo-N-methyl-2-nitroaniline obtained in the above step (1) into 20 milliliter of pyridine, further adding 5.0 g (35 mmol) benzoyl chloride, the resultant solution was refluxed with heating at the temperature of 90° C. under an atmosphere of argon gas for 7 hours. After completing the reaction, 200 milliliter of ethyl acetate was added and the resultant solution was washed with 10% HCL, with 10% $K_2CO_3$ and with a saturated solution of sodium chloride and then, dried with the use of magnesium sulfate. After filtration, the solvent was removed by distillation under reduced pressure and the residue was refined with silicagel column chromatography (hexane:ethyl acetate=10:1 at primary stage→2:1 from middle stage) resultantly obtaining 9.5 g of 4'-bromo-N-methyl-2'-amino-benzanilide as greenish white solids (yield: 96%).

(3) Synthesis of 4'-bromo-N-methyl-2'-amino-benzanilide

Dissolving 9.5 g (28 mmol) of 4'-bromo-N-methyl-2'-nitro-benzanilide obtained in the above step (2) into 100 milliliter of tetrahydrofuran, and during agitation under the atmosphere of argon gas and at room temperature, a solution provided by mixing 25 g (0.14 mmol) of sodium hydrosulfite into 90 milliliter of water was added. Further, adding 10 milliliter of methanol, the resultant solution was stirred for 3 hours. Subsequently, adding 100 milliliter of ethyl acetate and then, a solution provided by mixing 12 g (0.14 mmol) of sodium hydrogen carbonate and 125 milliliter of water was further added. The resultant solution was stirred for 1 hour, followed by extracting with ethyl acetate. After removing water layer, an organic layer was washed with 10% $K_2CO_3$ aqueous solution and with saturated solution of sodium chloride, followed by drying with the use of magnesium sulfate. After filtration, the solvent was removed by distillation under reduced pressure and 7.8 g of 4'-bromo-N-methyl-2'-amino-benzanilide was obtained as white solids (yield: 90%). The white solids were used in the next reaction as crude products.

(4) Synthesis of 5-bromo-1-methyl-2-phenyl-1H-benzimidazole

Suspending 7.8 g (26 mmol) of 4'-bromo-N-methyl-2'-amino-benzanilide obtained in the above step (3) into 50 milliliter of xylene, and adding 1.5 g (7.7 mmol) of p-toluenesulfonic acid 1 hydrate, the resultant solution was refluxed with heating for 7 hours. After completing the reaction, the resultant solution was filtered. Dissolving the resultant solids into methylene chloride, the resultant solution was washed with 10% $K_2CO_3$ aqueous solution and with a saturated solution of sodium chloride, and then, after drying with the use of magnesium sulfate, the solvent was removed by distillation. Washing the filtrate with 10% $K_2CO_3$ aqueous solution and with saturated solution of sodium chloride, and then, after drying with the use of magnesium sulfate, the solvent was removed by distillation. Combining the above two kinds of residues after removing by distillation, the resultant product was refined with silicagel column chromatography, 6.50 g of 5-bromo-1-methyl-2-phenyl-1H-benzimidazole was obtained as white solids (yield: 89%).

(5) Synthesis of 1-methyl-5-(10-naphthalene-2-yl-anthracene-9-yl)-2-phenyl-1H-benzimidazole (Compound (15-8))

Dissolving 1.5 g (5.6 mmol) of 5-bromo-1-methyl-2-phenyl-1H-benzimidazole obtained in the above step (4), 2.3 g (5.6 mmol) of 10-naphthalene-2-yl-anthracene-9-boronic acid and 0.12 g (0.11 mmol) of tetrakis (triphenylphosphine) palladium into 60 milliliter of 1,2-dimethoxyethane, adding 30 milliliter of 2.0M sodium carbonate aqueous solution, the resultant solution was refluxed with heating under an atmosphere of argon gas for 8 hours. After completion of the reaction, separation with filtration was carried out and resultant solids were washed with water, methanol and toluene, thereby obtaining greenish white solids. Re-crystallizing the greenish white solids with the use of toluene, 2.0 g of yellowish green solids were obtained (yield: 74%). As a result of mass spectrum (MS) analysis, it was recognized that the yellowish green solids were identified as the aimed substance and that m/e=510 for molecular weight of 510.21.

Synthesis Example 14

Synthesis of Compound (16-2)

(1) Synthesis of 5'-bromo-2'-(N-phenylamino)-picoline anilide

Suspending 2.3 g (19 mmol) of picolinic acid into 30 milliliter of 1,2-dichloroethane, adding 3.1 g (26 mmol) of thionyl chloride and 3 drops of N,N-dimethylformamide, the resultant solution was refluxed with heating for 3 hours. After completion of the reaction, the solvent was removed by distillation under reduced pressure, thereby obtaining picolyl chloride. Dissolving 5.0 g (17 mmol) of 4-bromo-2-nitrodiphenyl amine into milliliter of tetrahydrofuran, and during agitation under the atmosphere of nitrogen gas and at room temperature, a solution provided by mixing 14.9 g (85 mmol) of sodium hydrosulfite into 50 milliliter of water was added. Further, adding 4 milliliter of methanol, the resultant solution was stirred for 3 hours. Subsequently, adding 40 milliliter of ethyl acetate and then, a solution provided by mixing 2.9 g (34 mmol) of sodium hydrogen carbonate and 30 milliliter of water was further added. The resultant solution was stirred for 30 minutes, followed by extracting with ethyl acetate. After removing a water layer, an organic layer was washed with water and with a saturated solution of sodium chloride and dried with magnesium sulfate. Adding 2.7 g (40 mmol) of pyridine, further dropping a solution provided by mixing picolyl chloride and 25 milliliter of ethyl acetate, the resultant solution was stirred at room temperature for 5 hours. The solution was extracted with ethyl acetate, washed with 10% potassium carbonate aqueous solution and with saturated solution of sodium chloride successively, followed by drying with the use of magnesium sulfuric anhydride. Removing the solvent by distillation under reduced pressure, 3.1 g of 5'-bromo-2'-(N-phenylamino)-picoline anilide was obtained (yield: 49%).

(2) Synthesis of 5-bromo-1-phenyl-2-(2-pyridyl)-1H-benzimidazole

Suspending 3.1 g (8.4 mmol) of 5'-bromo-2'-(N-phenylamino)-picoline anilide obtained in the above step (1) into 30 milliliter of xylene, and adding 0.48 g (2.5 mmol) of p-toluenesulfonic acid 1 hydrate, the resultant solution was azeotropically dehydrated while refluxing with heating for 5 hours. The reacted solution was cooled down to room temperature, and the solvent was removed by distillation. Dissolving the resultant solid into ethyl acetate, and after sequentially washing with water, with 10% potassium carbonate aqueous solution and with saturated solution of sodium chloride, it was dried with the use of magnesium sulfuric anhydride, followed by removing the solvent by distillation under reduced pressure, 2.0 g of 5-bromo-1-phenyl-2-(2-pyridyl)-1H-benzimidazole was obtained (yield: 69%).

(3) Synthesis of 5-(10-naphthalene-2-yl-anthracene-9-yl)-1-phenyl-2-(2-pyridyl)-1H-benzimidazole Dissolving 2.0 g (5.8 mmol) of 5-bromo-1-phenyl-2-(2-pyridyl)-1H-benzimidazole obtained in the above step (2), 2.2 g (6.3 mmol) of 10-naphthalene-2-yl-anthracene-9-boronic acid and 0.13 g (0.11 mmol) of tetrakis (triphenylphosphine) palladium into 30 milliliter of 1,2-dimethoxyethane, adding 15 milliliter of 2.0M sodium carbonate aqueous solution, the resultant solution was refluxed with heating under an atmosphere of argon gas for 8 hours. After completion of the reaction, separation with filtration was carried out and resultant solids were washed with water, methanol and toluene, thereby obtaining 2.0 g of greenish white solids (yield: 61%). As a result of mass spectrum (MS) analysis, it was recognized that the greenish white solids were identified as the aimed substance and that m/e=573 for molecular weight of 573.22.

Example 1

Preparation of the Organic EL Device Employing the Compound of the Present Invention in an Electron Injecting Layer A glass substrate (manufactured by GEOMATEC Company) with a dimension of 25 mm×75 mm and 1.1 mm in thickness having an ITO transparent electrode was cleaned by application of ultrasonic wave in isopropyl alcohol for 5 minutes and then by exposure to ozone generated by ultraviolet light for 30 minutes. The glass substrate having the transparent electrode line which had been cleaned was adhered to a substrate holder of a vacuum vapor deposition apparatus. On the surface of the cleaned substrate at the side having the transparent electrode line, a film of N,N'-bis(N,N'-diphenyl-4-aminophenyl)-N,N-diphenyl-4,4'-diamino-1,1'-biphenyl (referred to as a "film of TPD232", hereinafter) having a thickness of 60 nm was formed in accordance with the resistance heating deposition method in a manner such that the formed film covered the transparent electrode. The formed film of TPD232 worked as the hole injecting layer. Subsequent to the film-forming of the film of TPD232, a film of 4,4'-bis[N-(1-naphthyl)-N-phenylamino]biphenyl (referred to as a "film of NPD", hereinunder) having a thickness of 20 nm was formed over the film of TPD232 in accordance with the resistance heating deposition method. The formed film of NPD worked as a hole transporting layer. Over the formed film of NPD, 4',4''-bis(2,2-diphenylvinyl)-9,10-biphenylanthracene (referred to as "DPVDPAN", hereinafter) having a thickness of 40 nm was further formed in accordance with the resistance heating deposition method. The formed film of DPVDPAN worked as the light emitting layer. Subsequent to the film-forming of the film of DPVDPAN, a film of Compound (1-7) of the present invention having a thickness of 10 nm was formed over the film of DPVDPAN in accordance with the vapor deposition method. The formed film of the compound (1-7) worked as the electron injecting layer. Thereafter, Li (the source of lithium: produced by SAES GETTERS Company) was binary vapor deposited and Compound (1-7):Li film having a thickness of 10 nm was formed as the electron injecting layer (or, the cathode) with the film-forming rate of 1.6 Å/second: 1 Å/minute. On the formed compound (1-7): Li film, metallic aluminum having the film thickness of 130 nm was vapor deposited to form a metal cathode and an organic EL device was prepared.

Example 2

Organic EL devices were prepared in similar manners as Example 1 except that Compound (4-2) was employed instead of Compound (1-7).

Examples 3 to 8

Preparation of the Organic EL Device Employing the Compound of the Present Invention in an Electron Injecting Layer A glass substrate (manufactured by GEOMATEC Company) with a dimension of 25 mm×75 mm and 1.1 mm in thickness having an ITO transparent electrode was cleaned by application of ultrasonic wave in isopropyl alcohol for 5 minutes and then by exposure to ozone generated by ultraviolet light for 30 minutes. The glass substrate having the transparent electrode line which had been cleaned was adhered to a substrate holder of a vacuum vapor deposition apparatus. On the surface of the cleaned substrate at the side having the transparent electrode line, a film of TPD232 having a thickness of 60 nm was formed in accordance with the resistance heating deposition method in a manner such that the formed film covered the transparent electrode. The formed film of TPD232 worked as the hole injecting layer. Subsequent to the film-forming of the film of TPD232, a film of NPD having a thickness of 20 nm was formed over the film of TPD232 in accordance with the resistance heating deposition method. The formed film of NPD worked as a hole transporting layer. Further, over the formed film of NPD, both styryl derivative PVDPAN and styryl amine derivative S1 (ionization potential Ip=5.3 eV, energy gap Eg=2.8 eV) were vapor deposited with a film thickness ratio of 40:2 to form a bluish light emitting layer having a thickness of 40 nm. Over the formed film, each film of the compound described in Table 1 was formed as an electron transporting layer having a film thickness of 20 nm. Thereafter, a film of LiF (the source of lithium: available from SAES GETTERS Company) having a thickness of 1 nm was further formed. On the formed thin film, metallic aluminum was vapor deposited to form a metal cathode having a thickness of 150 nm and an organic EL device was prepared.

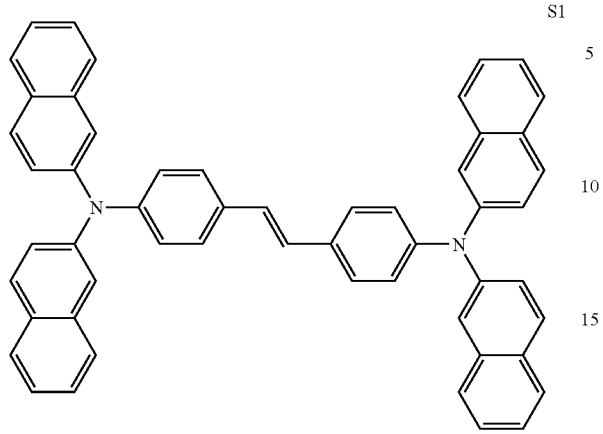

Comparative Example 1

An organic EL device was prepared in a similar manner as Example 1 except that Alq (aluminum complex of 8-hydroxyquinoline) was employed instead of Compound (1-7).

Comparative Example 2

An organic EL device was prepared in a similar manner as Example 1 except that Compound A below that is described in U.S. Pat. No. 5,645,948 was employed instead of Compound (1-7).

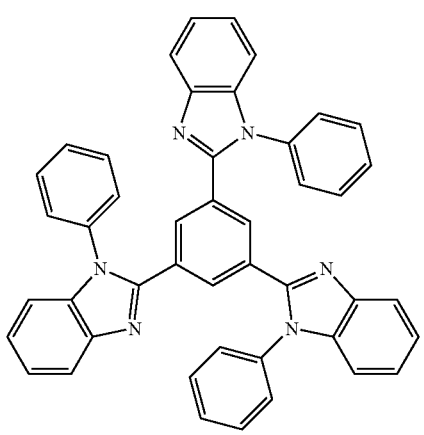

Comparative Example 3

An organic EL device was prepared in a similar manner as Example 1 except that Compound B below that is described in Japanese Unexamined Patent Application Laid Open No. 2002-38141 was employed instead of Compound (1-7).

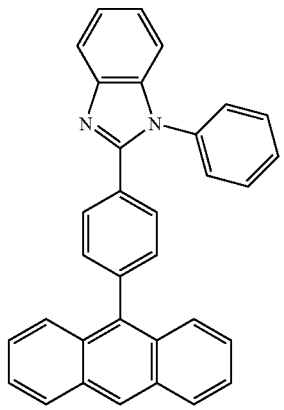

(Evaluation of the Organic EL Device)

The organic EL devices prepared in Examples 1 to 8 and in Comparative Examples 1 to 2 were subjected to measurements of luminance, current efficiency and chromaticity while applying DC voltages described in Table 1 below and further, colors of emitted light were observed. Further, the organic EL devices prepared in Examples 1 to 8 and in Comparative Examples 1 to 2 were subjected to measurements of half lifetime in the condition that luminence at primary stage was 500 nit. The results are shown in Table 1.

TABLE 1

| | Compound in Electron Injecting Layer | Voltage (V) | Current Density (mA/cm$^2$) | Luminance (nit) |
|---|---|---|---|---|
| Ex. 1 | 1-7 | 7.0 | 20.0 | 795 |
| Ex. 2 | 4-2 | 7.0 | 25.0 | 1,000 |
| Ex. 3 | 1-7 | 6.5 | 18.6 | 1,050 |
| Ex. 4 | 15-2 | 5.5 | 13.6 | 1,020 |
| Ex. 5 | 7-8 | 5.0 | 29.5 | 1,090 |
| Ex. 6 | 7-7 | 5.5 | 13.4 | 950 |
| Ex. 7 | 7-9 | 5.75 | 15.8 | 1,150 |
| Ex. 8 | 3-1 | 5.75 | 16.5 | 1,055 |
| Co. Ex. 1 | Alq | 7.0 | 13.0 | 500 |
| Co. Ex. 2 | Compound A | 7.0 | 7.4 | 185 |
| Co. Ex. 3 | Compound B | 7.0 | 15.0 | 600 |

| | Current Efficiency (cd/A) | Chromaticity (x, y) | Color of Light Emission | Half Lifetime (hours) |
|---|---|---|---|---|
| Ex. 1 | 4.0 | (0.144, 0.148) | Blue | 850 |
| Ex. 2 | 4.0 | (0.147, 0.156) | Blue | 1000 |
| Ex. 3 | 5.65 | (0.142, 0.145) | Blue | — |
| Ex. 4 | 7.50 | (0.142, 0.149) | Blue | — |
| Ex. 5 | 3.69 | (0.141, 0.147) | Blue | — |
| Ex. 6 | 7.09 | (0.143, 0.152) | Blue | — |
| Ex. 7 | 7.28 | (0.142, 0.148) | Blue | — |
| Ex. 8 | 6.40 | (0.143, 0.149) | Blue | — |
| Co. Ex. 1 | 3.8 | (0.149, 0.164) | Blue | 1000 |
| Co. Ex. 2 | 2.5 | (0.144, 0.148) | Blue | 30 |
| Co. Ex. 3 | 4.0 | (0.145, 0.153) | Blue | 20 |

It is apparently verified from the results in Table 1 that the compounds represented by general formulae (I) to (III) employed for an electron injecting layer enables to prepare the organic EL device with extremely enhanced luminance and extremely high current efficiency. Especially, it was verified that an organic EL device with an electron transporting layer employing the compound represented by general formulae (II) and (III) exhibits enhanced luminance particularly at low driving voltage, and that an organic EL device with an electron transporting layer employing the compound with alkyl group or pyridyl group as R¹, R² or R³ respectively in general formulae (I) to (III) also exhibits enhanced luminance at low driving voltage.

INDUSTRIAL APPLICABILITY

In accordance with the present invention, an organic EL device achieving elevation of luminance and of efficiency in light emission even under low driving voltage is obtainable by an employment of the derivative of heterocyclic compound having nitrogen atom for at least one layer composing organic compound layers of the organic EL device.

What is claimed is:
1. A derivative of heterocyclic compound having nitrogen atom represented by following general formula (I):

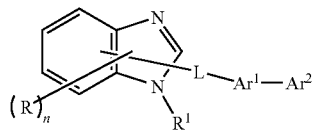
(I)

wherein R represents a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent;

n represents an integer of 0 to 4;

R¹ represents an aryl group having 6 to 60 carbon atoms which may have a substituent, a pyridyl group which may have a substituent, a quinolyl group which may have a substituent, an alkyl group having 1 to 20 carbon atoms which may have a substituent, or an alkoxy group having 1 to 20 carbon atoms and may have a substituent, with the proviso that the alkyl group is not propyl;

L represents an arylene group having 6 to 60 carbon atoms which may have a substituent, a pyridinylene group which may have a substituent, a quinolinylene group which may have a substituent, or a fluorenylene group which may have a substituent, with the proviso that any substituent of L is not heteroaryl;

Ar¹ represents a pyridinylene group which may have a substituent, a quinolinylene group which may have a substituent, or an arylene group selected from the following general formulae (1), (2), (4) to (10), (11) to (21), and (25), with the proviso that any substituent of Ar¹ is not heteroaryl;

wherein general formulae (1), (2), (4) to (10) are:

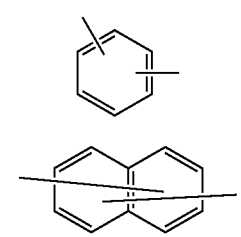

(1)

(2)

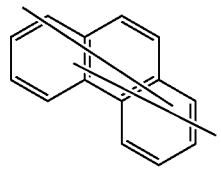
(4)

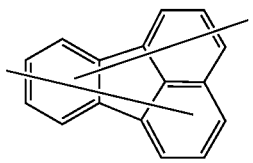
(5)

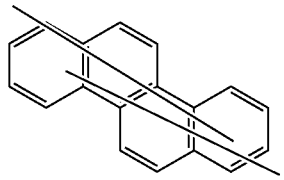
(6)

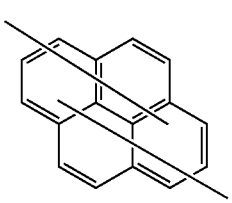
(7)

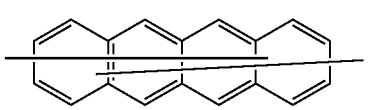
(8)

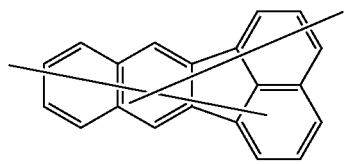
(9)

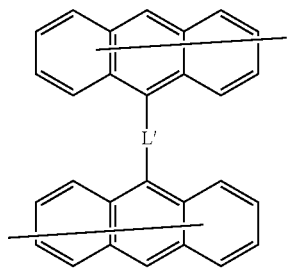
(10)

wherein each ring group may be bonded with a substituent selected from the group consisting of a halogen atom, an alkyl group having 1 to 20 carbon atoms which may have a substituent, an alkoxy group having 1 to 20 carbon atoms which may have a substituent, an aryloxy group having 6 to 40 carbon atoms which may have a substituent, an aryl group having 6 to 40 carbon atoms which may have a substituent; and when there is a plurality of substituents on the ring group, the substituents may be the same or different from each other; and L' represents a single bond or a group selected from the following groups:

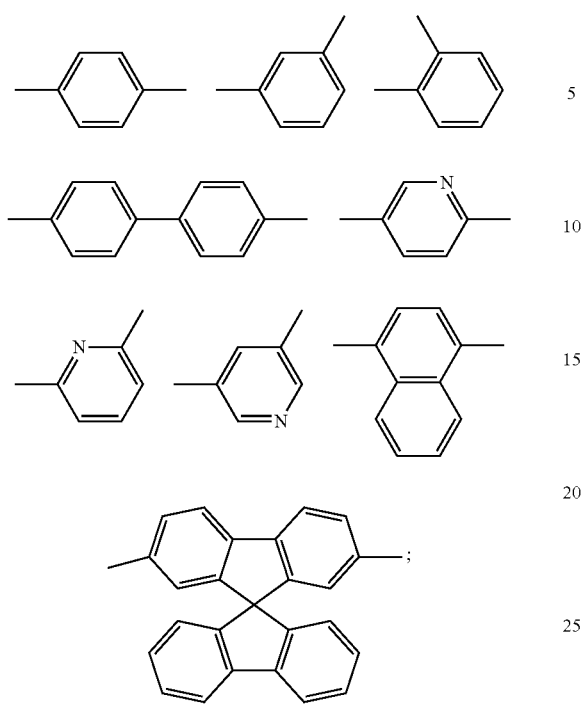
and general formulae (11) to (21), and (25) are:
(11)
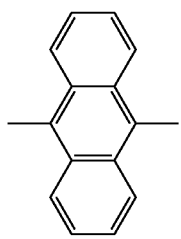
(12)
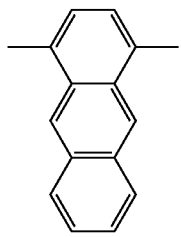
(13)
(14)
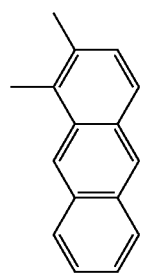
(15)
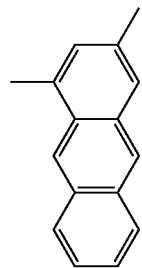
(16)
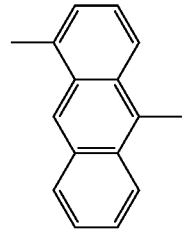
(17)
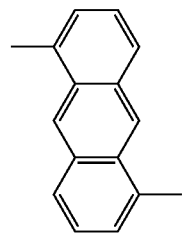
(18)
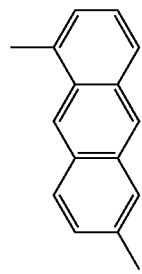
(19)
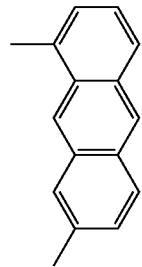

(20)
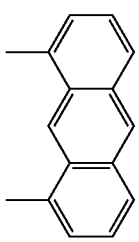

(21)
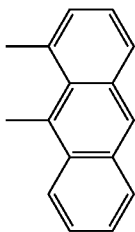

(25)
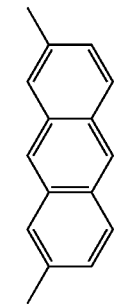

wherein each condensed ring group may be bonded with a substituent selected from the group consisting of a halogen atom, an alkyl group having 1 to 20 carbon atoms, an alkoxy group having 1 to 20 carbon atoms, an aryloxy group having 6 to 40 carbon atoms; and when there is a plurality of substituents on the condensed ring group, the substituents may be the same or different from each other;

$Ar^2$ represents an aryl group having 6 to 20 carbon atoms which may have a substituent, a pyridyl group which may have a substituent, a quinolyl group which may have a substituent, an alkyl group having 1 to 20 carbon atoms which may have a substituent, or an alkoxy group having 1 to 20 carbon atoms which may have a substituent, with the proviso that any substituent of $Ar^2$ is not heteroaryl.

2. The derivative of heterocyclic compound having nitrogen atom according to claim 1, wherein L is at least one group selected from the following groups:

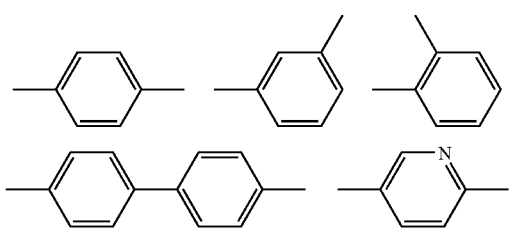

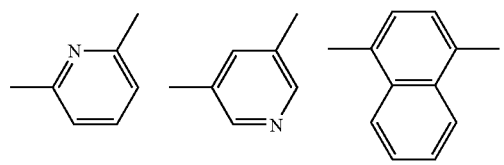

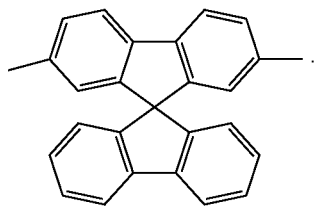

3. The derivative of heterocyclic compound having nitrogen atom according to claim 1, wherein $Ar^2$ is a ring group selected from the following groups:

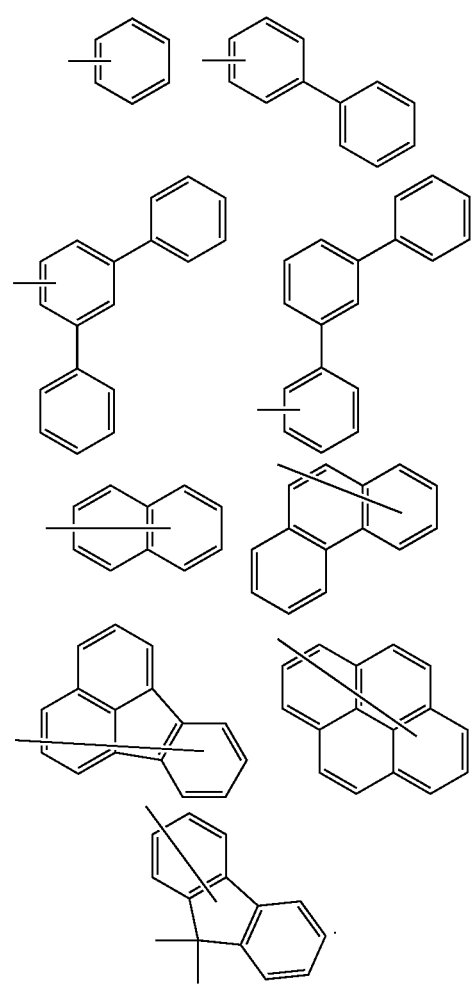

4. An organic electroluminescence device comprising at least one organic compound layer containing a light emitting layer sandwiched between a pair of electrodes, wherein the device contains the derivative of heterocyclic compound having nitrogen atom according to claim 1 among the compound layer.

5. The organic electroluminescence device according to claim 4, wherein said derivative of heterocyclic compound having nitrogen atom is contained in a light emission area.

6. The organic electroluminescence device according to claim 4, wherein said derivative of heterocyclic compound having nitrogen atom is contained in the light emitting layer.

7. The organic electroluminescence device according to claim 4, wherein said derivative of heterocyclic compound having nitrogen atom is employed for at least one of an electron injection material and an electron transport material.

8. The organic electroluminescence device according to claim 7, wherein a layer comprising said at least one of the electron injection material and the electron transport material further comprises a reductive dopant.

9. The organic electroluminescence device according to claim 8, wherein said reductive dopant is at least one selected from the group consisting of alkali metal, alkaline earth metal, rare earth metal, oxide of alkali metal, halide of alkali metal, oxide of alkaline earth metal, halide of alkaline earth metal, oxide of rare earth metal, halide of rare earth metal, organic complexes of alkali metal, organic complexes of alkaline earth metal and organic complexes of rare earth metal.

* * * * *